(12) United States Patent
Davis et al.

(10) Patent No.: US 6,216,549 B1
(45) Date of Patent: Apr. 17, 2001

(54) COLLAPSIBLE BAG SEDIMENT/WATER QUALITY FLOW-WEIGHTED SAMPLER

(75) Inventors: Broderick Davis, Vicksburg; Carnet Wayne O'Neal, Terry, both of MS (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 0 days.

(21) Appl. No.: 09/209,267

(22) Filed: Dec. 11, 1998

(51) Int. Cl.[7] ............................................. G01N 1/20
(52) U.S. Cl. .................................. 73/863.52; 73/863.43
(58) Field of Search ............................ 73/863.52, 863.43, 73/170.29, 170.31, 170.32, 170.33, 170.34

(56) References Cited

U.S. PATENT DOCUMENTS

| | | | |
|---|---|---|---|
| 4,302,974 | * 12/1981 | Niskin | 73/864.62 |
| 4,606,233 | * 8/1986 | Burney | 73/864.63 |
| 4,888,999 | * 12/1989 | Kozak | 73/864.05 |
| 5,339,676 | * 8/1994 | Johnson | 73/863.52 X |
| 5,693,894 | * 12/1997 | Jobson | 73/863.03 |
| 5,996,427 | * 12/1999 | Mosek et al. | 73/863.52 X |

* cited by examiner

Primary Examiner—Thomas P. Noland
(74) Attorney, Agent, or Firm—E. Philip Koltos

(57) ABSTRACT

A collapsible bag sampler comprises a top section; a bottom section connected to the top section; a tail section having fins, which tail section is fitted onto the top section; a nose section with tray, which tray supports a flexible bag; a nozzle holder; a nozzle holder insert in the top section to hold the nozzle; and a flexible bag attached to the outside of the rear of the nozzle holder. Because the bag container is flexible and contains substantially no air, there are no limitations due to air compressibility, meaning the depth to which the sampler could be used would be limited only by the size of the intake nozzle and the volume of the bag. The transit rate is limited only by the apparent approach angle of the nozzle facing into the stream velocity as it makes its vertical descent and ascent (0.4 times the stream velocity). The sampler has a useful range of from 2.0 ft/sec to approximately 10 ft/sec stream velocities.

11 Claims, 21 Drawing Sheets

FIG. 9 Effect of pressure equalization hole

COLLAPSIBLE BAG SEDIMENT/WATER QUALITY FLOW-WEIGHTED SAMPLER

FIELD OF THE INVENTION

The present invention relates to a collapsible bag sampler to sample sediment and/or water for water quality analysis from flowing bodies of water.

BACKGROUND OF THE INVENTION

Dredging operations in navigable waterways are based upon the rate of sediment deposition. The study of the rate of sediment deposition can be greatly enhanced by collecting unbiased water-sediment samples from rivers and streams.

The life expectancy of a water reservoir is determined by the rate at which it is filled with sediment from the rivers and streams that feed it. In order to determine the rate of sediment deposition in a water reservoir, it is necessary to have a means to take accurate and reliable samples from the flowing waters that feed the reservoir.

The U.S. Government is currently involved in comprehensive studies of the quality of the rivers in the United States. For the past 30 years the U.S. Geological Survey has conducted the National Stream Quality Accounting Network (NASQAN). The NASQAN provides information for tracking water quality conditions in major U.S. rivers. Another federal program is the National Water Quality Assessment (NAWQA) program, conducted by the U.S. Geological Survey. The NAWQA program is designed to assess the status and trends in the quality of the nation's ground- and surface-water resources and to develop an understanding of the major factors that affect water quality conditions.

In the early days of fluvial-sediment investigations, each investigator or agency responsible for investigation developed methods and equipment individually as needed. It became apparent that reliable and consistent data could not be obtained unless equipment, collection methods, and analytical methods were standardized. To overcome this difficulty, representatives of several Federal agencies met in 1939 to form an Interdepartmental Committee to standardize sediment data-collection equipment and methods and analytical equipment. The committee was reorganized in 1956 to its present structure as the Federal Interagency Sedimentation Project (FISP) (Edwards and Glysson, 1988).

Since its initiation in 1939, FISP has published more than 50 reports dealing with nearly all aspects of measurement and analysis of fluvial sediment movement. FISP has also set up several criteria for the design and construction of suspended-sediment samplers:

1. Water must enter the sampler nozzle isokinetically. In isokinetic sampling, water approaching the sampler nozzle of the sampler undergoes no change in speed or direction as it enters the nozzle.

2. The sampler nozzle must be permitted to reach a point as close to the streambed as is physically possible.

3. Disturbance of the flow pattern of the stream must be minimized, especially at the nozzle.

4. The sampler must be adaptable to support equipment already in use for streamflow measurement.

5. The device must be as simple and maintenance free as possible.

6. The sampler must accommodate a standard bottle size, i.e., 1-pint (473 ml) glass, 1-quart (946 ml) glass, 1-liter plastic, or 3-liter plastic.

Isokinetic samplers are divided into two categories according to how they sample: those that are depth-integrating and those that are point-integrating. A depth-integrating sampler is designed to accumulate a water-sediment sample from a stream vertical at such a rate that the velocity in the intake nozzle is essentially equal to the incident stream velocity while transiting the vertical at a uniform rate (FISP, 1952). The resulting water-sediment sample collected is proportional to the instantaneous stream velocity at the locus of the intake nozzle and therefore will be representative of the sediment load in the vertical. A simple depth-integrating sampler fills while it is being lowered from the water surface to the streambed and while being raised to the surface again.

At any instant during the operation of a depth-integrating sampler, the air mass in a rigid container is a function of the hydrostatic head and the volume of water-sediment collected. As the sampler is lowered into a stream, sufficient water must enter the container to compress instantaneously the inside air so that its pressure balances the external hydrostatic head according to Boyle's law. For the water-sediment inflow in the nozzle to be equal to the stream velocity, the rate of air volume contraction due to increasing hydrostatic pressure must not exceed the normal volume rate of liquid inflow. As a result, the sampler must be lowered and raised in the water column at a rate such that these two factors are balanced to avoid the water-sediment mixture being forced into the sampler at a velocity greater than the ambient stream velocity. This vertical rate is know as the transit rate. Studies have shown that its value must not exceed 0.4 times the stream velocity due to the apparent approach angle of the nozzle facing into the stream as the sampler makes its vertical descent and ascent (FISP, 1952).

Other studies of the filling characteristics of the rigid-bottle container have shown that the maximum distance the sampler can travel through the water column and still sample is isokinetically is 34 ft at sea level (FISP, 1952). Since the depth-integrating sampler collects water from the instant it enters the stream, the maximum theoretical stream depth that can be sampled is half of this distance, or approximately 17 feet. General field practice limits the use of depth-integrating samplers to 15 feet (Edwards and Glysson, 1988).

FISP has designed depth-integrating rigid-bottle samplers that have been used for many years. These are designated as the U.S. DH-48, a 1-pint hand held sampler; the U.S. DH-59, a 1-quart hand line sampler; and the U.S. D-77, a 3-liter cable-suspended sampler.

Rigid-bottle samplers are limited to a depth of 15 feet. Additionally, rigid bottle samplers are limited in transit rate due to the air compressibility problems associated with rigid-bottle samplers.

Suspended-sediment samplers using a collapsible bag have been investigated as an improvement over the U.S. series of depth-integrating samplers. Several investigators have researched collapsible bag samplers. Two early models were developed by Gluschkoff (FISP, 1940) and by the Rhine Works Authority (FISP, 1940). The Gluschoff sampler, developed in Russia, consists of several balloon-shaped bags, each fitted with a nozzle. The nozzles were mounted on a vertical staff and oriented horizontally in the same direction. When sampling, the staff was inserted into the stream with the nozzles facing downstream and with the bags devoid of air. The staff was then twisted so that the nozzles faced upstream. The bags simultaneously collected point-integrated samples at preselected depths. The staff was again twisted so that the nozzles faced downstream, pinching off any further inflow. The staff was carefully lifted out of the water and the samples removed. The major problem with the arrangement was that the bags were unprotected and had to be handled very carefully.

The Rhine Works Authority sampler consisted of a latex balloon, a nozzle, and a metal frame with a tail fin. When sampling, a pinch clamp located at the neck of the balloon was operated by an auxiliary line to allow flow into the balloon. The sampler was not streamlined, and the requirement for an auxiliary line limited the use of the sampler.

Stevens and others (Stevens et al, 1980) fabricated 1-gallon and 2-gallon samplers using plastic bags. The samplers consisted of a wide-mouth, perforated, rigid container enclosed in a cage-like metal frame attached above a sounding weight. The head of the frame supported a plastic intake nozzle and swung open to permit the plastic container to be removed. When the head was closed, the end of the nozzle extended slightly into the mouth of the container and the container sealed against a gasket. An adjustable rubber stop at the rear of the sampler held the container in place. The perforations in the container were 0.75 in diameter holes arranged in three partial rings of six holes each on the underside of the container at different lengths. In addition, there was a large opening in the side of the container just below its neck. During sampling, this opening was covered with a loose fitting plastic sleeve. For sampling, a collapsed, pre-shaped, flexible, plastic bag was placed inside the rigid container. The neck of the flexible bag was stretched over the neck of the rigid container, and the whole unit placed into the sampler. The sampler was of limited use at stream velocities above 3 ft/sec, was cumbersome to operate, and had an unsampled zone of approximately 18 inches.

Szalona (1982) conducted another investigation into the use of a bag sampler. His approach was to modify the U.S. D-77 sampler. The sampler was equipped with a 3-liter plastic bottle, nozzle cap and nozzle, and used a commercially available food storage bag. Holes were drilled in various locations of the bottle to enable quick flooding of the bottle. Various combinations of vents and deflectors were added to the U.S. D-77 sampler to facilitate isokinetic sampling. The sampler had limited use at stream velocities above 3 ft/sec. However, its sampling capacity is limited to approximately 2.5 liters. Some difficulty was also encountered trying to remove the bag filled with sample through the small opening of the bottle mouth. Additional testing by FISP and experience by field personnel has shown that if the collapsible bag is not placed correctly inside the container, the sampler will not sample at all.

In a recent study of contaminants in the Mississippi River, Robert Meade used an 8-liter frame-type bag sampler similar to that described by Stevens (Meade). This sampler consisted of a perforated 8-liter plastic container with a U.S. D-77 sampler cap and nozzle secured inside a metal frame. The metal frame was suspended above a sounding weight. A collapsed 8-liter perfloroalkoxy (PFA) bag was placed inside the plastic container. Analysis of the sampling data showed that the sampler collected water-sediment at a rate that approached isokinetic (ideal plus or minus 15 pct) in only about half of the samples.

Jobson, in U.S. Pat. No. 5,693,894, discloses a fluid controlled isokinetic fluid sampler comprising an inflatable bag provided within a hollow fluid-tight housing which is filled with water or other appropriate liquid. An inlet tube permits a sample of a flowing fluid to be introduced into the inflatable bag from the exterior of the housing to inflate the bag within the housing. A pump is provided to pump the water from within the housing through an outlet tube to the exterior of the housing at a flow rate proportional to the flow rate of the flowing fluid.

Kozak, in U.S. Pat. No. 4,888,999, discloses a tank bottom sampling device comprising an outer cylindrical body having a suspending handle and a central opening through which a piston assembly is positioned. As the device is lowered into a tank bottom, an extension at the bottom of the piston contacts the tank bottom and the piston moves upward to allow liquid to flow into the sampling device. This device is not designed to be used in flowing waters.

Inking, in U.S. Pat. No. 4,302,974, discloses a water sampling device comprising a pliable container or bag initially mounted in a deflated condition on a framework. The framework includes sealing means for securing the pliable container with at least a portion of the container in a partially rolled condition to seal an opening in the container. The framework further includes opening means for unrolling the container to expose the opening to the container at the desired water sampling depth. A pair of wing members mounted to the framework spread apart the sides of the container to draw water through the unsealed opening. After the container has been substantially filled with water, resealing means of the framework rolls the container back up to seal the container at the sampling depth.

Burney, in U.S. Pat. No. 4,606,233, discloses a bag sampler comprising a rigid plastic frame and a flexible polyethylene bag. The frame holds the bag open during filling and allows it to close without using rigid moving parts. The frame comprises a bag-retaining flange bonded to a cylindrical central core attached to four heavy struts which support a large hoop frame at the front end thereof. The central core is a sealed hollow chamber, which is penetrated by an internal sampling tube with polypropylene compression tube fittings at both ends. The sampling tube passes through the central core, extends a few centimeters behind the retaining flange, and is held in place by both the front and rear compression fittings. A plugged port in the forward end of the central core allows the change to be ballasted with water to achieve neutral buoyancy. A plurality of holes provide attachment points for a towing harness.

Unfortunately, many of the bag samplers described above were not consistent in sampling. Sometimes they would obtain a sample and sometimes they would not, for no apparent reason. Additionally, they would only collect a sample volume approximately 80 percent of their rated volume. They had a large unsampled zone (the distance from the streambed to the intake nozzle). They would not sample effectively at stream velocities below approximately 3 ft/sec.

SUMMARY OF THE INVENTION

It is an object of the present invention to overcome the deficiencies in the prior art.

It is another object of the present invention to provide a clean water sampler that would collect water for trace element analysis at depths greater than 15 feet.

It is a further object of the present invention to provide an isokinetic sampler to collect unbiased sediment and water quality samples in rivers and streams.

It is another object of the present invention to provide a sediment/water quality sampler using a collapsible bag as the sample container.

It is still another object of the present invention to provide a sediment/water quality sampler limited in the depth to which it could be used only by its nozzle diameter and sample volume.

It is a further object of the present invention to provide a sediment/water quality sampler which is not limited in transit rate use due to the air compressibility problems associated with rigid bottle samplers.

According to the present invention, a collapsible bag sampler is provided which has an internal cavity in the sampler body that contains a flexible bag. Because the bag is flexible and contains substantially no air, there are no limitations due to air compressibility, meaning the depth to which the sampler could be used would be limited only by the size of the intake nozzle and the volume of the bag. The transit rate is limited only by the apparent approach angle of the nozzle facing into the stream velocity as it makes its vertical descent and ascent (0.4 times the stream velocity).

The sampler of the present invention includes a sampler body designed with a cavity inside to contain the bag. A holder is designed so that a nozzle is attached to one end and a bag to the other end. A small pressure-equalization hole in the holder and vent holes in the sampler body ensure that the pressure inside and outside the bag was always equal. Since the hydrostatic pressures would always be equal, the only acting force would be the velocity head due to the stream velocity and a small venturi effect caused by vent holes with deflectors. As a result, the sampler should collect water-sediment at very near isokinetic rate at a wide range of stream velocities. This velocity head, coupled with vents in the sampler body to give a venturi effect, would be sufficient to allow the bag to open as it collected water-sediment. The vent holes would also serve to quickly evacuate the air in the cavity and flood it with water, then allow the water in the cavity to be evacuated as the bag filled with water-sediment.

DETAILED DESCRIPTION OF THE INVENTION

Figure 1A:
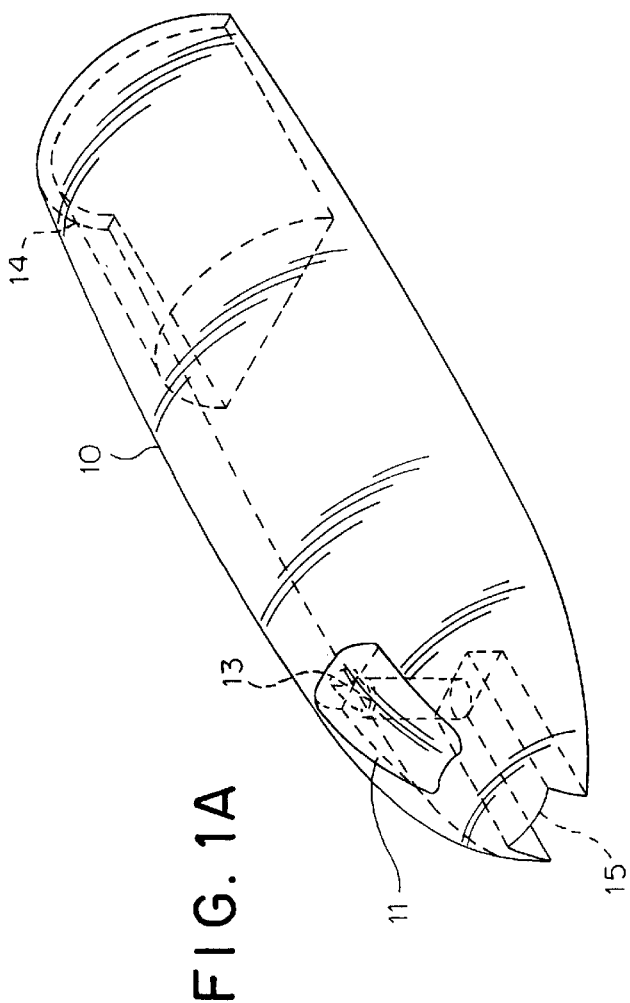
FIG. 1A is an isometric view of the top section of a sampler according to the present invention.
Figure 1B:
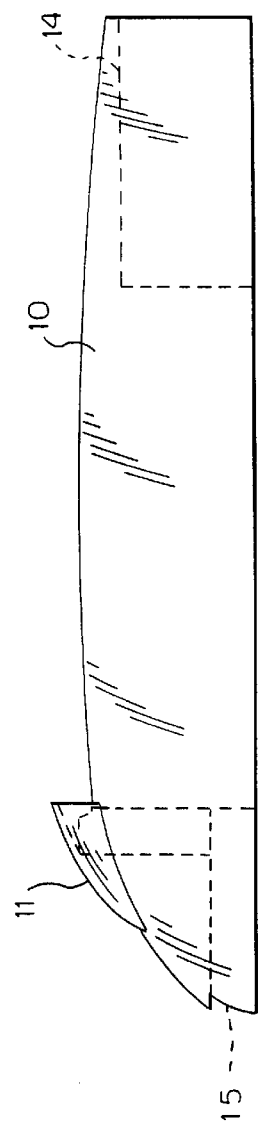
FIG. 1B is a side view of the top section of a sampler according to the present invention.
Figure 1C:
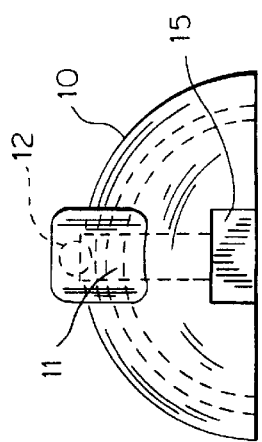
FIG. 1C is a front view of the top section of a sampler according to the present invention.

The sampler of the present invention is composed of several parts, including a top section, a bottom section, a tail section, a nose section with tray, a nozzle holder, and a nozzle holder insert. The top section is shown in FIGS. 1A, 1B, and 1C. The top section 10 is made of a heavy material and provides most of the weight to the sampler. A slot 11 is milled into the front of the top section to accept the nozzle holder insert. A first small diameter hole 12 is drilled toward the front of the top section to aid in evacuating air and water from the sampler bag cavity. The first 12 hole is drilled under a deflector that is part of the casting. A second small diameter hole 13 is drilled through the back of the deflector to intersect the first hole. This deflector creates a venturi effect that aids in allowing the bag to open, as well as evacuating air and water from the bag cavity. A half-cylinder shaped hole 14 is cast into the rear of the top section to facilitate attachment of the tail section.

Figure 2A:
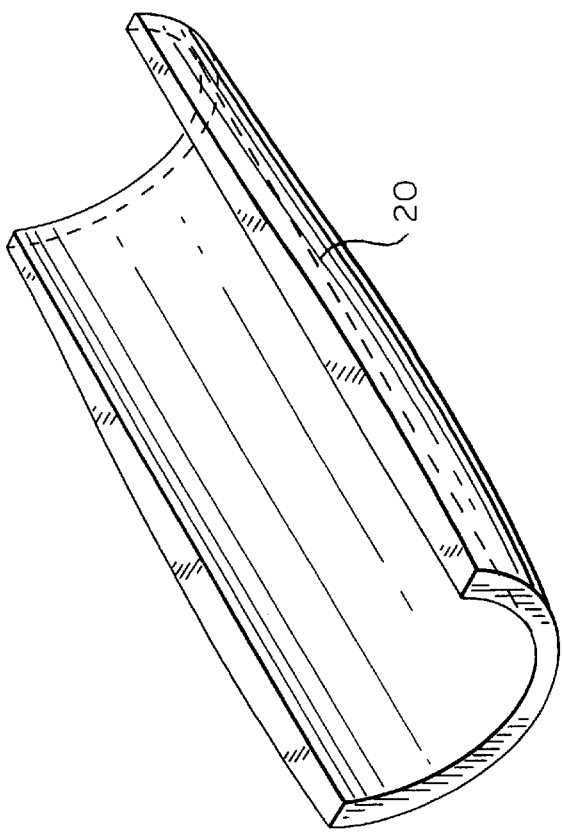
FIG. 2A is an isometric view of the bottom section of a sampler according to the present invention.
Figure 2C:
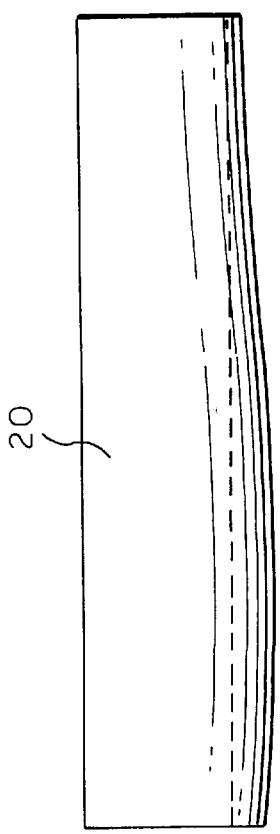
FIG. 2C is an end view of the bottom section of a sampler according to the present invention.
Figure 2B:
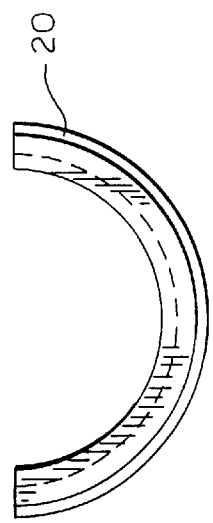
FIG. 2B is a side view of the bottom section of a sampler according to the present invention.

FIGS. 2A, 2B, and 2C show the bottom section 20 of the sampler. The bottom section may be made of a lighter material than the top section, as it is only the top section that is required to provide weight to the sampler. However, if a heavier version of the sampler is required, both the bottom and the nose sections can be made from the same type of heavy material as the top section. The bottom section 20 mates with the top section 10 to form a bag cavity inside the sampler. The bottom section 20 is fastened to the top section 10 using any conventional fastening means, including screws, adhesive, straps, and other types of fasteners.

Figure 3A:
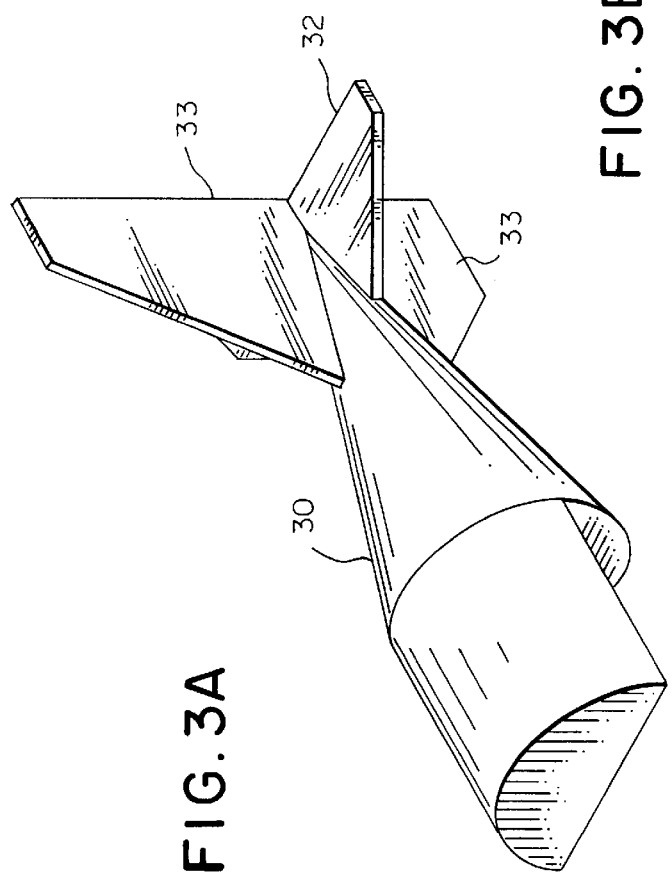
FIG. 3A is an isometric view of the tail section of a sampler according to the present invention.
Figure 3B:
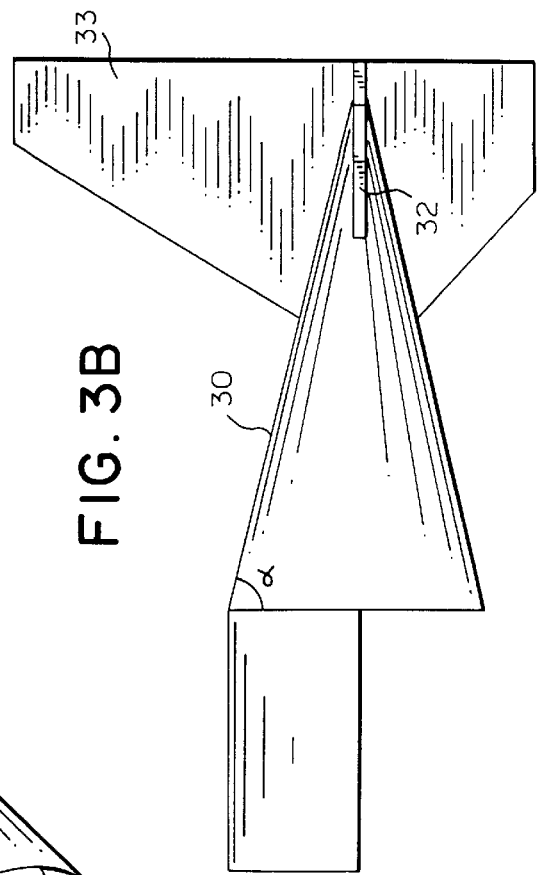
FIG. 3B is a side view of the tail section of a sampler according to the present invention.
Figure 3C:
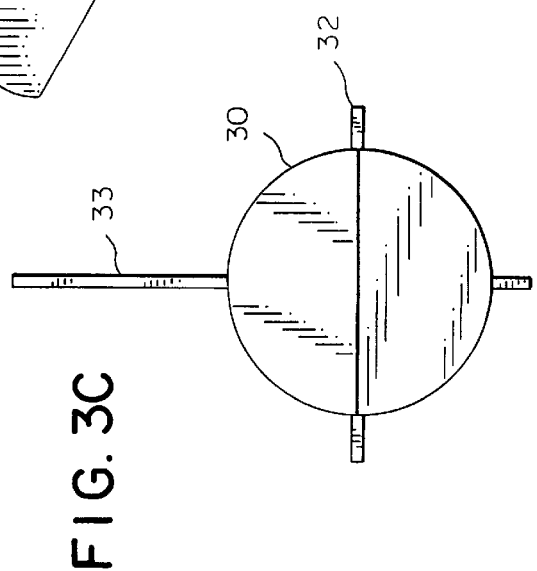
FIG. 3C is a front view of the tail section of a sampler according to the present invention.

The tail section 30, shown in FIGS. 3A, 3B, and 3C, is made of a light material such as synthetic plastics. The tail section comprises a half-cylinder section that fits inside the cast hole in the top section for attachment. Of course, any suitable means can be used for attaching the tail section to the top section of the sampler. The tail section is tapered at an angle α of about 6 degrees from the rear of the half-cylinder section. Horizontal 32 and vertical 33 fins made from relatively thin flexible material are welded to the tail section body, and the tail section is attached to the top section using any conventional fastening means, including screws, adhesive, straps, and other types of fasteners. The tail section can be tapered at an angle α of from about 3 to about 9 degrees from the rear of the half-cylinder section.

Figure 4A:
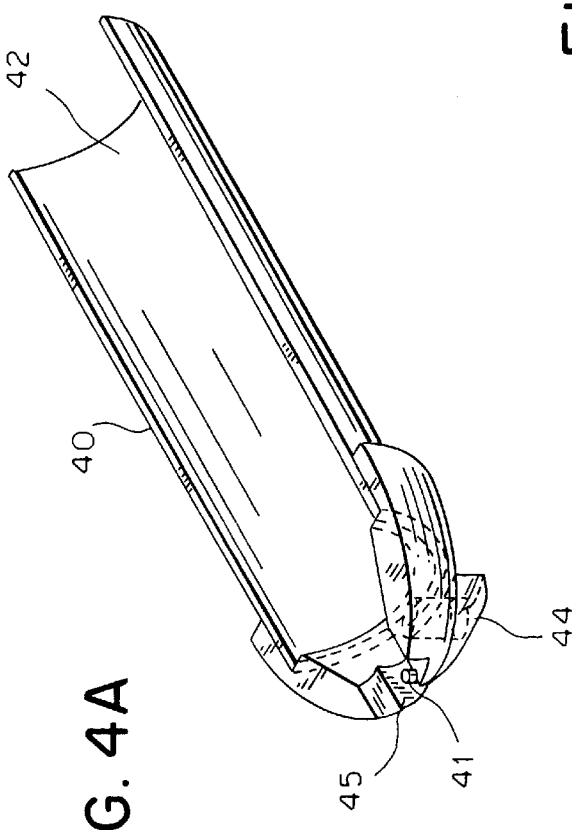
FIG. 4A is an isometric view of the nose section with tray of a sampler according to the present invention.
Figure 4B:
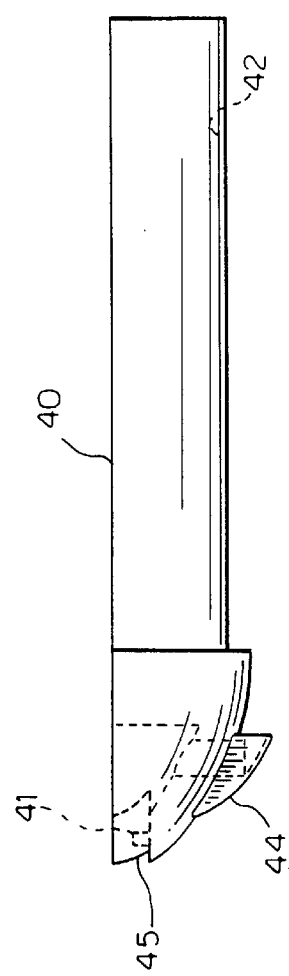
FIG. 4B is a side view of the nose section with tray of a sampler according to the present invention.
Figure 4C:
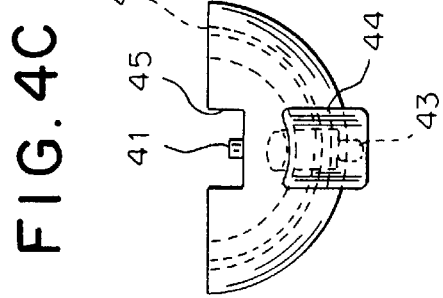
FIG. 4C is a front view of the nose section with tray of a sampler according to the present invention.

FIGS. 4A, 4B, and 4C show the nose section 40, which is made of a rigid material and has a slot 41 milled in the front that matches the slot in the top section for the nozzle holder insert. It is also fitted with a tray 42 that is made by halving length-wise a piece of tubing. The tray slides into the cavity formed by the bottom section and is designed to support the bag. The nose section is also vented with a hole 43 and deflector 44 that is similar to the one in the top section.

Figure 5B:
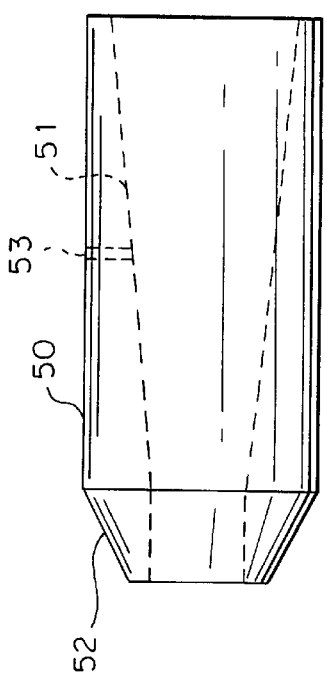
FIG. 5B is a side view of a nozzle holder of the sampler.
Figure 5A:
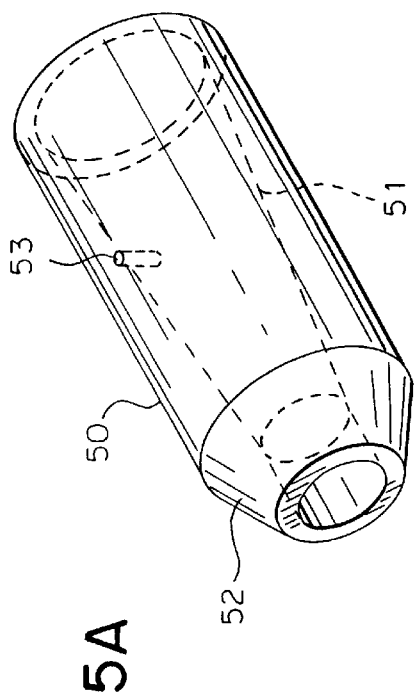
FIG. 5A is an isometric view of a nozzle holder of the sampler.
Figure 5C:
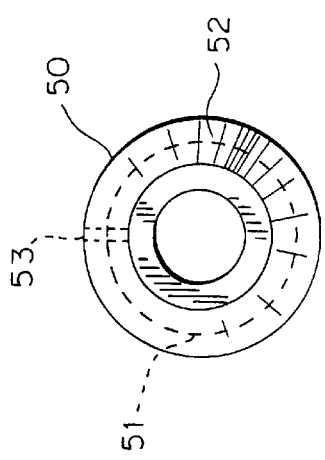
FIG. 5C is a front view of a nozzle holder of the sampler.

The nozzle holder 50 is shown in FIGS. 5A, 5B, and 5C. The nozzle holder 50 is made from a lightweight material. The inside 51 of the nozzle holder tapers outwardly from the front of the nozzle holder to the rear of the nozzle holder. The front outside part 52 of the nozzle holder is tapered and has a pressure equalization hole 53 drilled therein. This equalization hole ensures that the pressure inside the bag is equal to the pressure outside the bag, thereby insuring isokinetic sampling. The bag is attached to the outside of the rear of the nozzle holder.

Figure 6B:
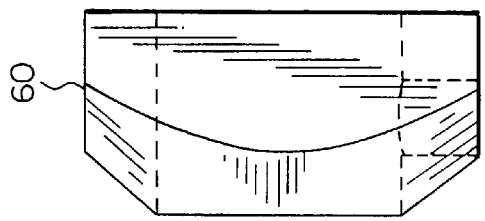
FIG. 6B is a side view of a nozzle holder insert of the sampler.
Figure 6A:
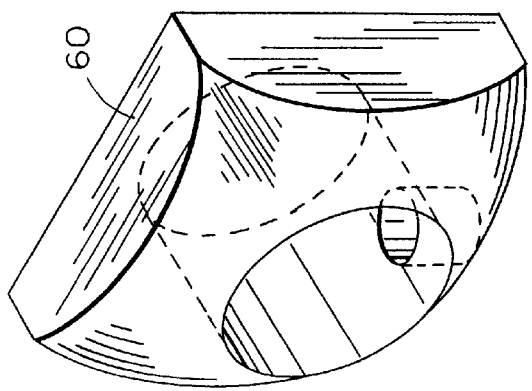
FIG. 6A is an isometric view of a nozzle holder insert of the sampler.
Figure 6C:
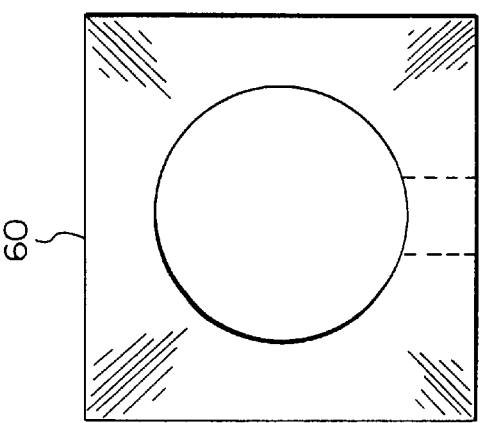
FIG. 6C is a front view of a nozzle holder insert of the sampler.

FIGS. 6A, 6B, and 6C show the nozzle holder insert 60. The nozzle holder insert 60 fits milled slots 15, 45 in the top section and the nose section, respectively. The bag opening is secured to the nozzle holder with any conventional fastening means.

Figure 7A:
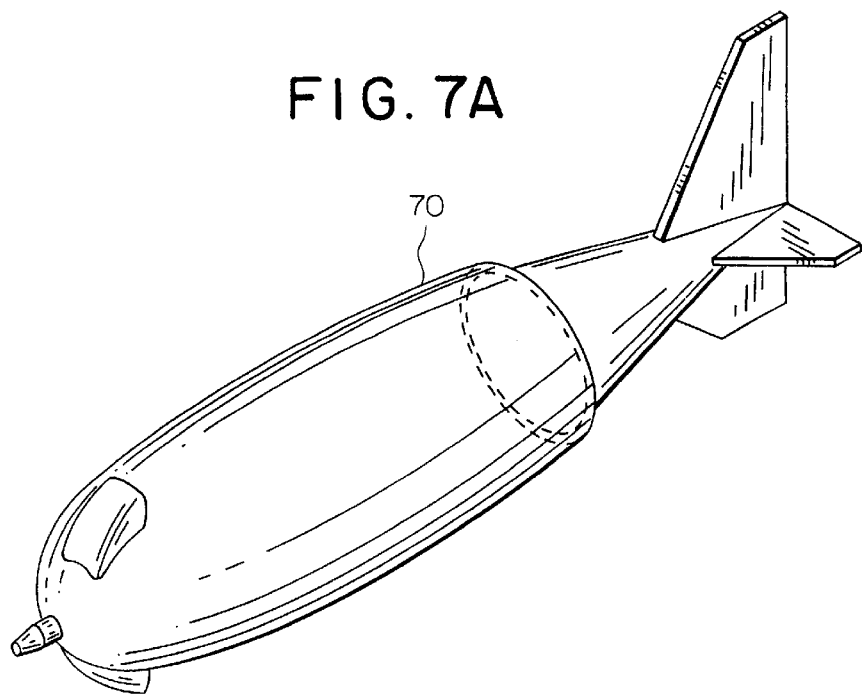
FIG. 7A is an isometric view of the assembled sampler according to the present invention.
Figure 7B:
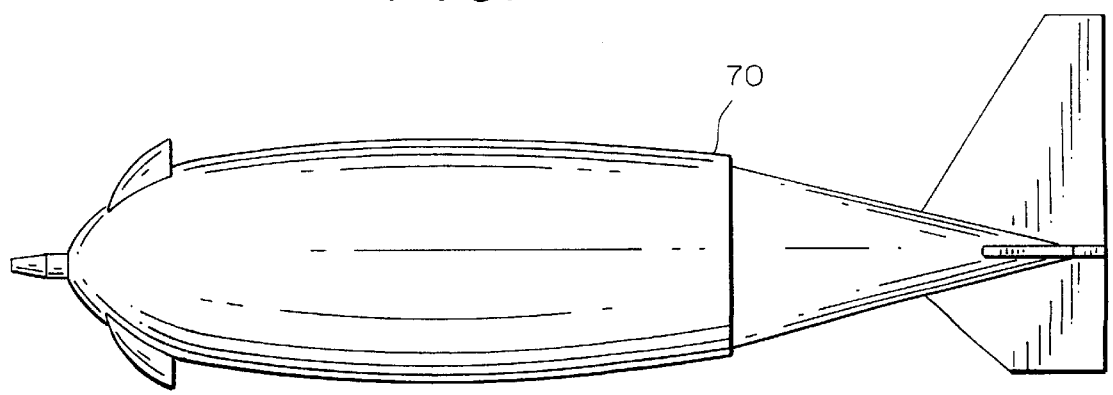
FIG. 7B is a side view of the assembled sampler according to the present invention.

The assembled sampler 70 is shown in FIGS. 7A and 7B. All of the metal parts can be covered with a protective coating to prevent contamination of water quality samples caused by touching base metal parts. The material used to make the tail section has a density of somewhat less than 1.00 g/cc, the density of water, so that it is neutrally buoyant in water. Regardless of the material or design construction, the apparent density of the tail must be approximately 1.0 g/cc in water so that it is neutrally buoyant in water, i.e., it could be made of metal with a sealed hollow chamber giving it an effective density of 1.0 in water. This allows the hanger bar of the sampler to be placed at a point at which the tail hangs lower than the nose of the sampler in air. When the sampler touches the water, the tail hits first, which forces the sampler quickly to orient facing into the stream. Once the sampler is completely submerged, the neutrally buoyant tail along with the horizontal fins causes the sampler to "swim" horizontally.

In one embodiment of the invention, the top section is 22.5 inches long and weighs approximately 100 pounds. A slot is milled into the front to accept the nozzle holder insert. A first hole one inch in diameter is drilled toward the front of the top section to aid in evacuating air and water from the sampler bag cavity. The first hole is drilled under a deflector that is part of the casting. A second hole, 0.625 inch in diameter, is drilled through the back of the deflector to intersect the first hole. This deflector creates a venturi effect that aids in allowing the bag to open, as well as evacuating air and water from the bag cavity. A 6 inch diameter half-cylinder shaped hole 6 inches deep is cast into the rear of the top section to facilitate attachment of the tail section.

FIG. 2 shows the bottom section of the sampler. The bottom section is a cast aluminum shell 16.5 inches long that mates with the top section to form a bag cavity inside the sampler. In this example, the bottom section is fastened to the top section with 0.25 inch Allen head machine screws. When Allen head machine screws are used as the fastening means, the top section is drilled and tapped to accept the machine screws.

The tail section, shown in FIG. 3, is made of high density polyethylene (HDPE). The tail has a half-cylinder section approximately 6 inches in diameter and 6 inches in length, that fits inside the cast hole in the top section for attachment. The total length of the tail section is 18.5 inches. The tail is tapered at an angle of about 13.5 degrees from the rear of the half-cylinder section. Horizontal and vertical fins made from 0.25 inch thick HDPE sheet are welded to the tail section body, and the tail section is attached to the top section with machine screws.

The nose section is made of cast aluminum and has a slot milled in the front that matches the slot in the top section for the nozzle holder insert. It is also fitted with a plastic tray that is made by halving length-wise a piece of six inch diameter clear plastic tube. The tray is 18 inches long and extends from 1 to 2 inches into the nose section. The nose section is vented with a 1 inch diameter hole and deflector similar to the one in the top section.

The nozzle holder is made from tetrafluoroethylene (TFE) and is 3 inches long and 1.25 inch in diameter. It has a 0.5 inch diameter hole drilled 0.5 inch deep in the front to accept the nozzle. The inside of the nozzle holder tapers outwardly from the back of the nozzle hole to the rear of the holder. The front outside part of the nozzle holder is tapered and has a pressure equalization hole drilled therein. The bag is attached to the outside of the rear of the nozzle holder.

The front part of the nozzle holder is tapered to a diameter of 0.75 inch. It also has a 0.0625 inch diameter pressure equalization hole.

The nozzle holder insert is made of plastic and fits milled slots in the top section and the nose section. The nozzle holder insert is 2 inches square and has a 1.25 inch diameter hole drilled therein to accept the nozzle holder. The bag used for testing is 4.61 inch in diameter by 24 inches long by 0.002 inch thick cylindrical PFA bag. The bag opening is secured to the nozzle holder with a plastic cable tie, although any conventional fastening means can be used to secure the bag opening to the nozzle holder.

All of the metal parts can be covered with a protective coating to prevent metal contamination during water quality sampling caused by touching base metal parts. In the embodiment described above, the sampler is approximately 35 inches long and weighs about 130 pounds. The sample volume is three liters. The HDPE used in the tail section has a density of 0.95 g/cc.

Experimental

A testing program was conducted to determine the effects of different design parameters that led to the final design. Tests were also performed to determine the isokinetic sampling capabilities of the final design over a range of stream velocities with different size nozzles. Test work was conducted in a flume at the Army Corps of Engineer Waterways Experiment Station located in Vicksburg, Miss. The flume had a cross section of three feet wide by three feet deep, and a straight section approximately 60 feet long. It had an adjustable tailgate to aid in control of water velocity. Water was supplied to the flume by two 24 cfs pumps and one 10 cfs pump, which may be operated in any combination. A small lake served as the water reservoir, and water from the flume was recirculated. The flume was capable of water velocities up to approximately 5 ft/sec. A Price type AA current meter with a Current Meter digitizer model number CMD 1.7 was used to measure flume velocity. The meter had been previously calibrated by the U.S. Geological Survey, Office of Surface Water's Hydraulics Laboratory located at Stennis Space Center in Bay St. Louis, Miss. A set of nozzles designed for use with a current rigid-bottle sampler was modified and calibrated for the tests. These nozzles had intake diameters of 0.1875 in, 0.25 in, and 0.3125 in.

Tests were conducted at three velocities, approximately 2, 3.65, and 5 ft/sec. The test procedure was as follows:

Three velocity measurements were made in succession and averaged for the flume velocity. This procedure was repeated after three samples were taken so that after every three observations the flume velocity was measured.

At a minimum, three replicates (samples taken) were conducted at each of five to seven volume levels of from 500 to 3000 mL. This resulted in up to 21 observations for each parameter effect.

Raw data, including sample volume, time of collection, flume velocity, and nozzle diameter were entered into a computer spread sheet which calculated the sampling efficiency for each observation. The sampling efficiency was considered the velocity of the water through the nozzle divided by the water velocity as measured in the flume. The water velocity through the nozzle was calculated from the volume of water collected and the elapsed time of collection, and making the appropriate calculation using the cross sectional area of the nozzle.

A sampling efficiency of 1.0 indicated that the sampler was sampling isokinetically. Tests conducted and reported in FISP Report 5 (FISP, 1941) show that minimal error in sediment concentration is incurred as long as the sampling efficiency is 1.0 plus or minus 0.15. Szalona (1982) also reports an acceptable efficiency of 1.0 plus or minus 0.15.

Many design parameters were tested to determine the optimal design for a sampler that would collect a full three liters at a range of stream velocities. The four major parameters were venting, nozzle placement, nozzle holder configuration, and bag configuration. Venting configurations tested were no vents, one vent in the top, one vent in top and one in the bottom, two vents in the top and two vents in the bottom, vents with and without deflectors, and venting in the rear of the sampler.

Figure 8:
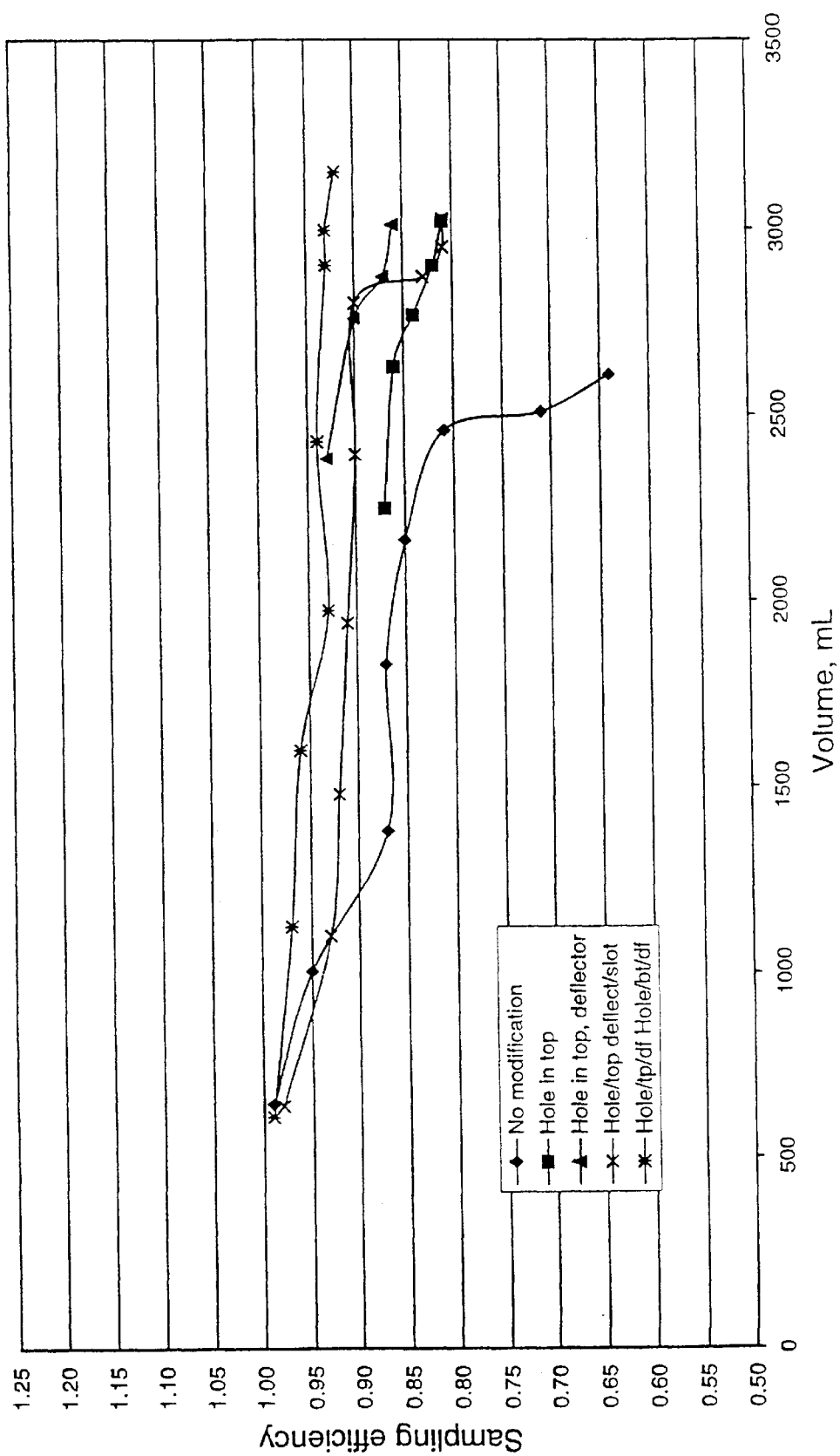
FIG. 8 shows the effects of various configurations of vent holes in the sampler body.

FIG. 8 shows the results of some of the tests on venting effects using a 0.25 inch diameter nozzle at 5 ft/sec flume velocity. The four conditions were: no vents; vent hole in the top; vent hole in the top with deflector; vent hole in the top with deflector and interior vent slots, and hole in the top and bottom with deflectors. As can be seen in FIG. 8, the case of no venting resulted in unacceptable sampling efficiency. In fact, the sampler would not collect more than approximately 2600 mL of water with no venting. In the cases with a hole in the top, a hole in the top with the deflector, and a hole in the top with a deflector and interior vent slots, sampling efficiencies were acceptable. However, it was clearly evident that a hole in the top with a deflector and a hole in the bottom with a deflector resulted in the collection of a sample of more than 3000 mL and a sampling efficiency of 0.92 to 0.99. The vent holes aided in rapid evacuation of air and influx of water into the sampler cavity around the outside of the sampler bag. This was necessary to help balance the pressures so that the only acting force was the velocity head created by the stream velocity. The deflectors over the holes created a slight venturi effect that aided in removing the water in the sampler cavity around the outside of the bag as the bag filled and allowed the bag to expand unrestricted as it filled with sample.

The bags used for the sampler were sized to have a volume nearly equal to the volume of the sampler cavity. They were PFA bags cylindrical in shape and 4.61 inch in diameter by 24 inches long. Tests were conducted with bags that were shortened to 19, 20, 21, 22, and 23 inches long. Tests were also conducted with bags that were modified to have a neck shaped like a bottle with a 1.5 inch diameter opening. The shorter bags and the modified bags showed no improvement over the 24 inch long cylindrically shaped bag.

Another parameter tested was nozzle placement. Placements tested were centerline, 0.5 inch above centerline, and 2.5 inches above centerline. In other tests the nozzle was extended 3, 5, and 7 inches in front of the sampler. Test results showed that the sampler performed best with the nozzle located at the centerline with no extension.

Even after all of the previously discussed parameters had been optimized, it was difficult to sample isokinetically at the low flume velocity of 2 ft/sec. This also was a problem with previously tested bag samplers, as they would not sample isokinetically at a flume velocity of less than 3 ft/sec.

Figure 9:
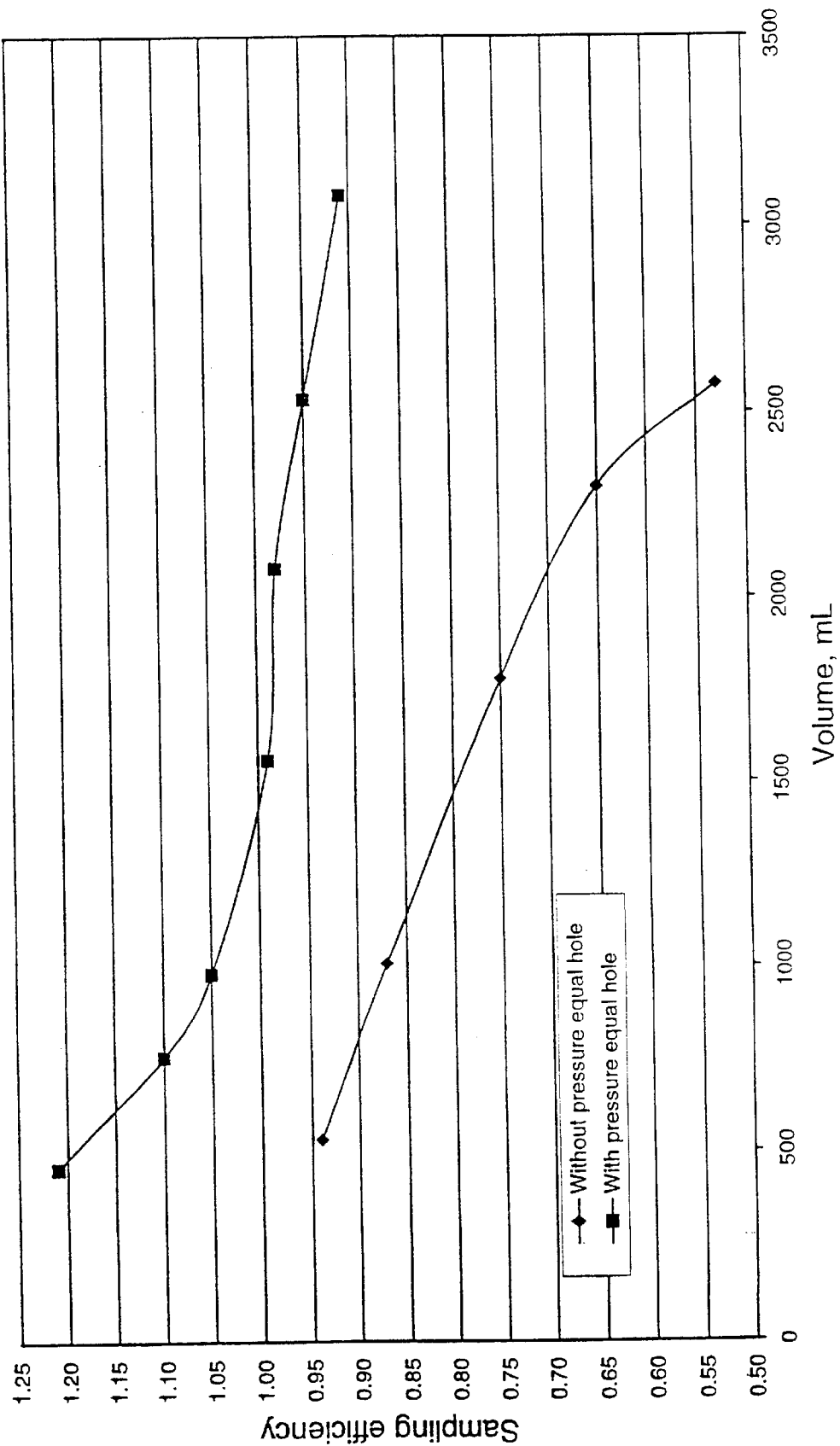
FIG. 9 shows the effects of the pressure equalization hole.

For the sampler to sample isokinetically, the pressure inside the bag, outside the bag in the sampler cavity, and the hydrostatic pressure outside the sampler must be very nearly equal so that the only acting force is the velocity head produced by the stream. To ensure that these pressures were balanced, a small pressure equalization hole (0.0625 inch in diameter) was drilled into the nozzle holder slightly in front of the point at which the bag was attached to the holder. FIG. 9 shows that the effect of the pressure equalization hole using a 0.25 inch diameter nozzle at 2 ft/sec flume velocity was significant. Without the hole, the sampling efficiency was not even close to being acceptable, and the sampler would not collect more than approximately 2600 mL. With the hole, the sampler collected more than 3000 mL. Except for the initial volume collected, the sampling efficiency was 0.91 to 1.10, which was well within the acceptable range.

Figure 10:
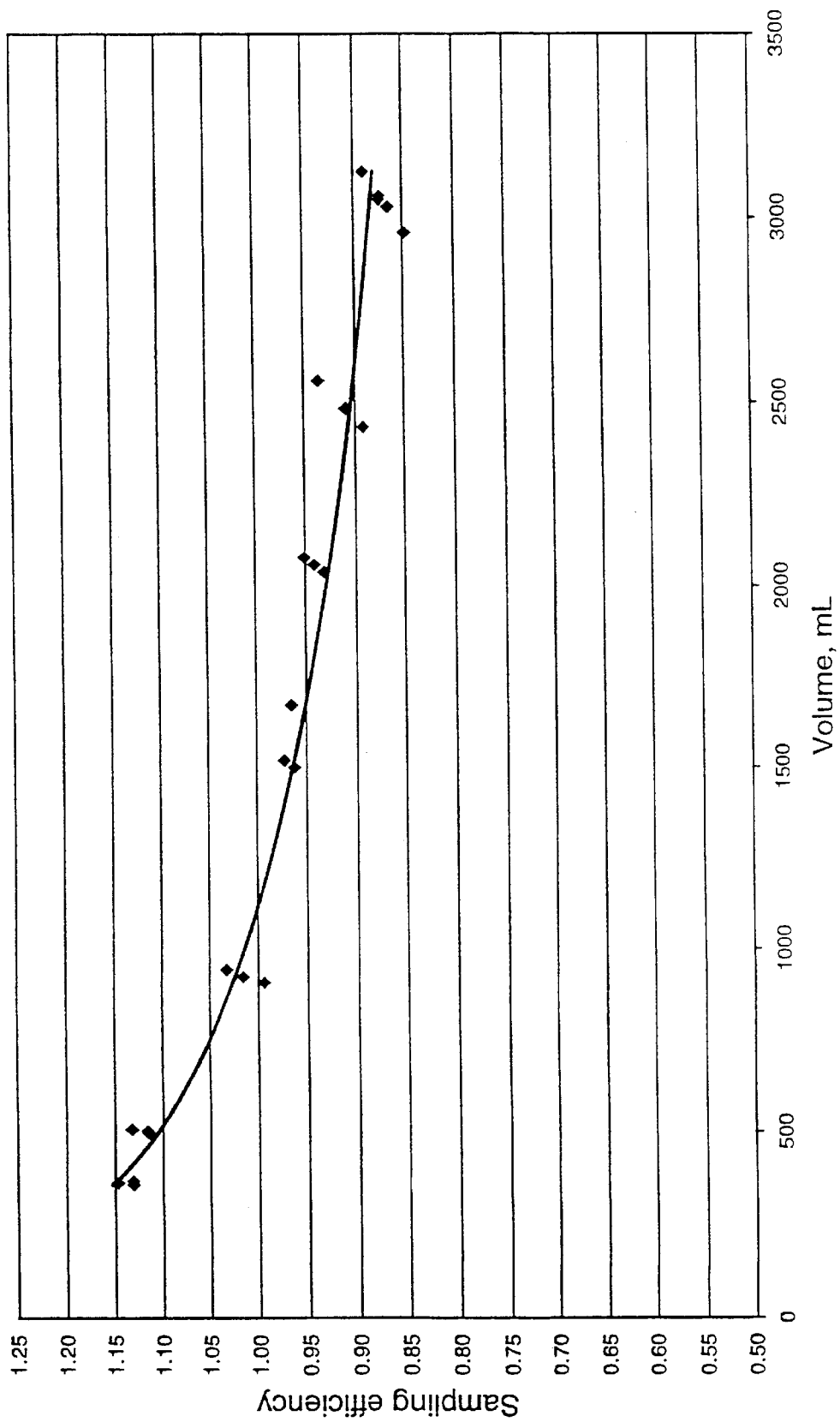
FIG. 10 shows the sampling efficiency of a sampler with a 0.1875 inch diameter nozzle at 2 ft/sec flume velocity.
Figure 11:
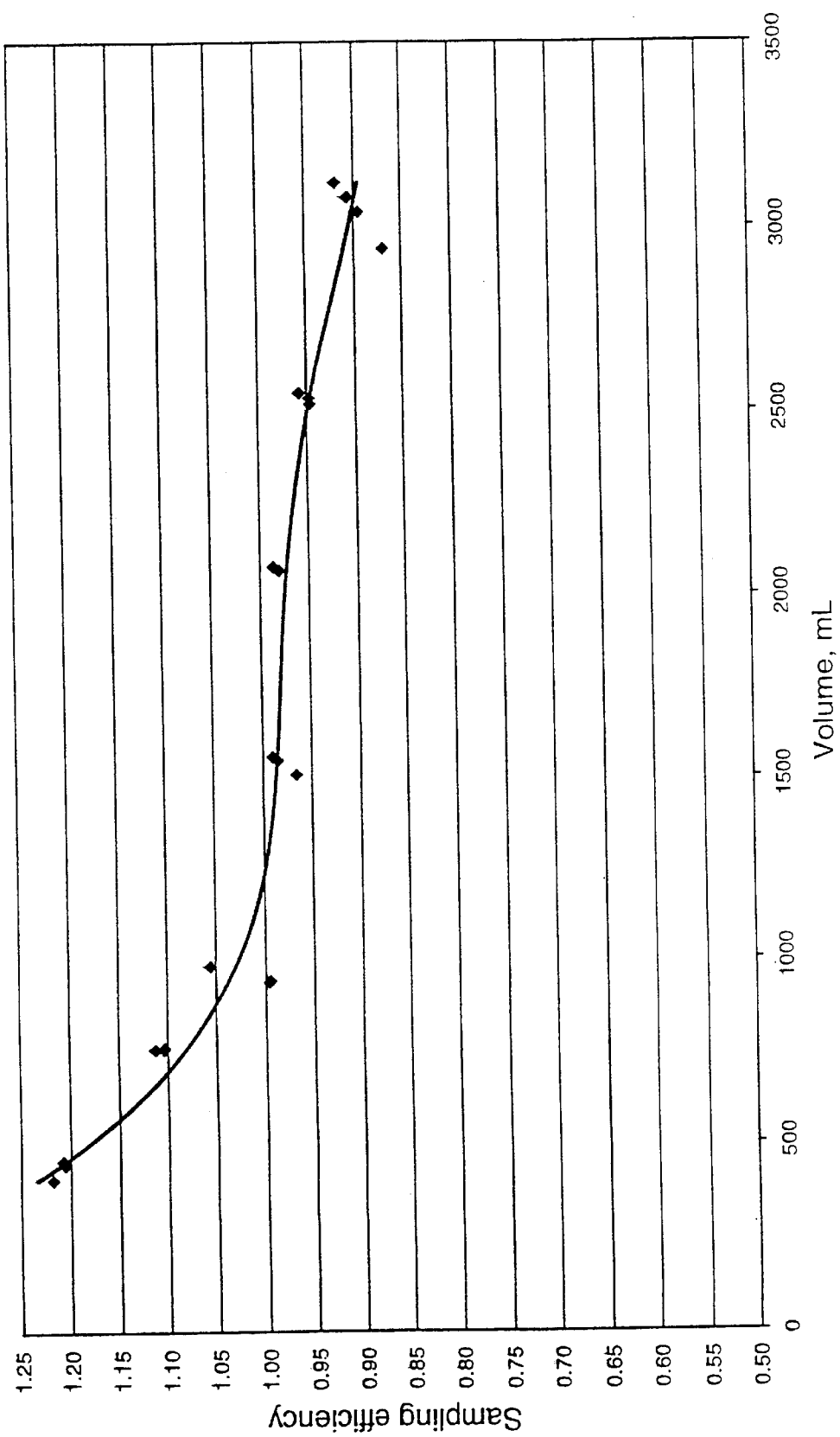
FIG. 11 shows the sampling efficiency of a sampler with a 0.25 inch diameter nozzle at 2 ft/sec flume velocity.
Figure 12:
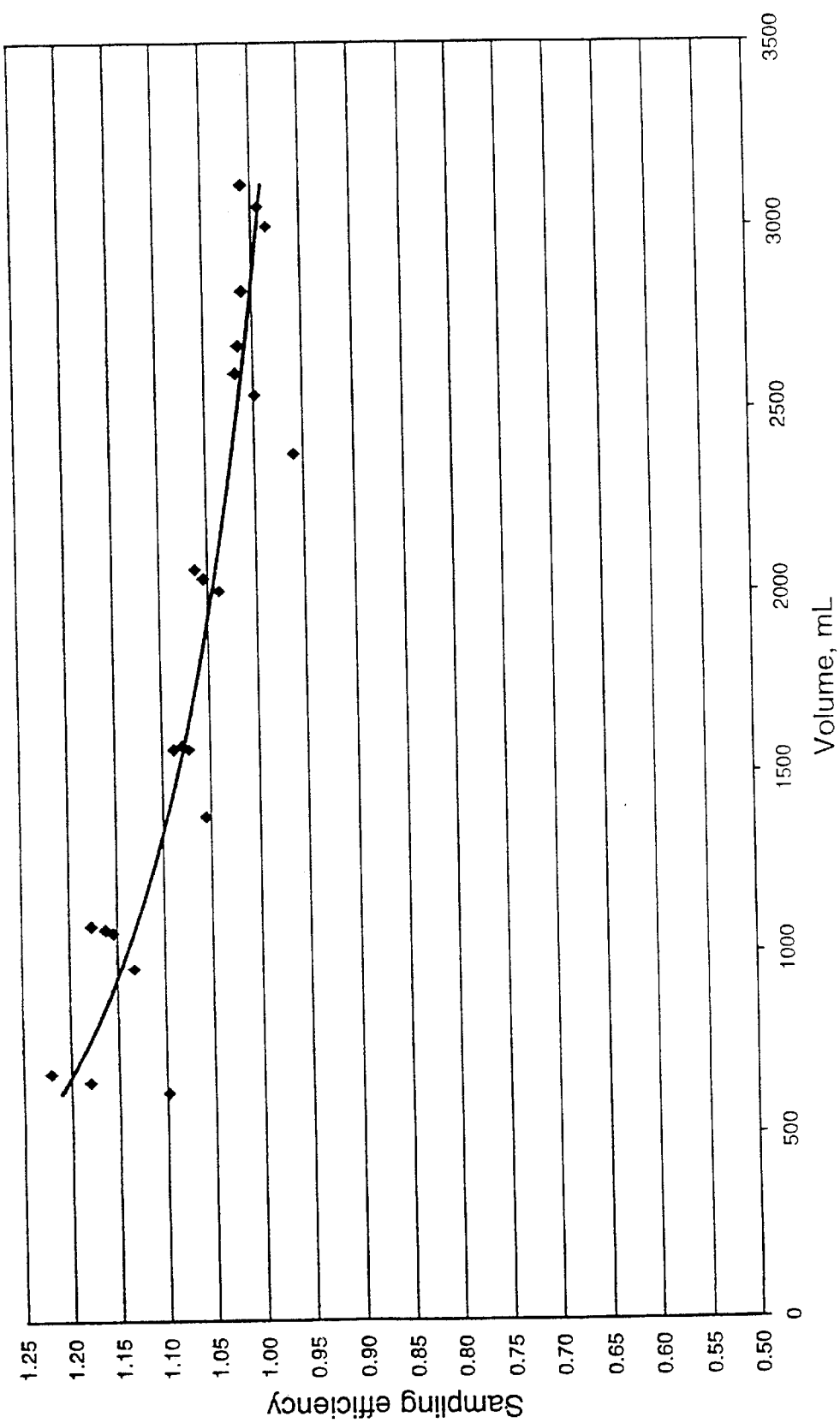
FIG. 12 shows the sampling efficiency of a sampler with a 0.3125 inch diameter nozzle at 2 ft/sec flume velocity.
Figure 13:
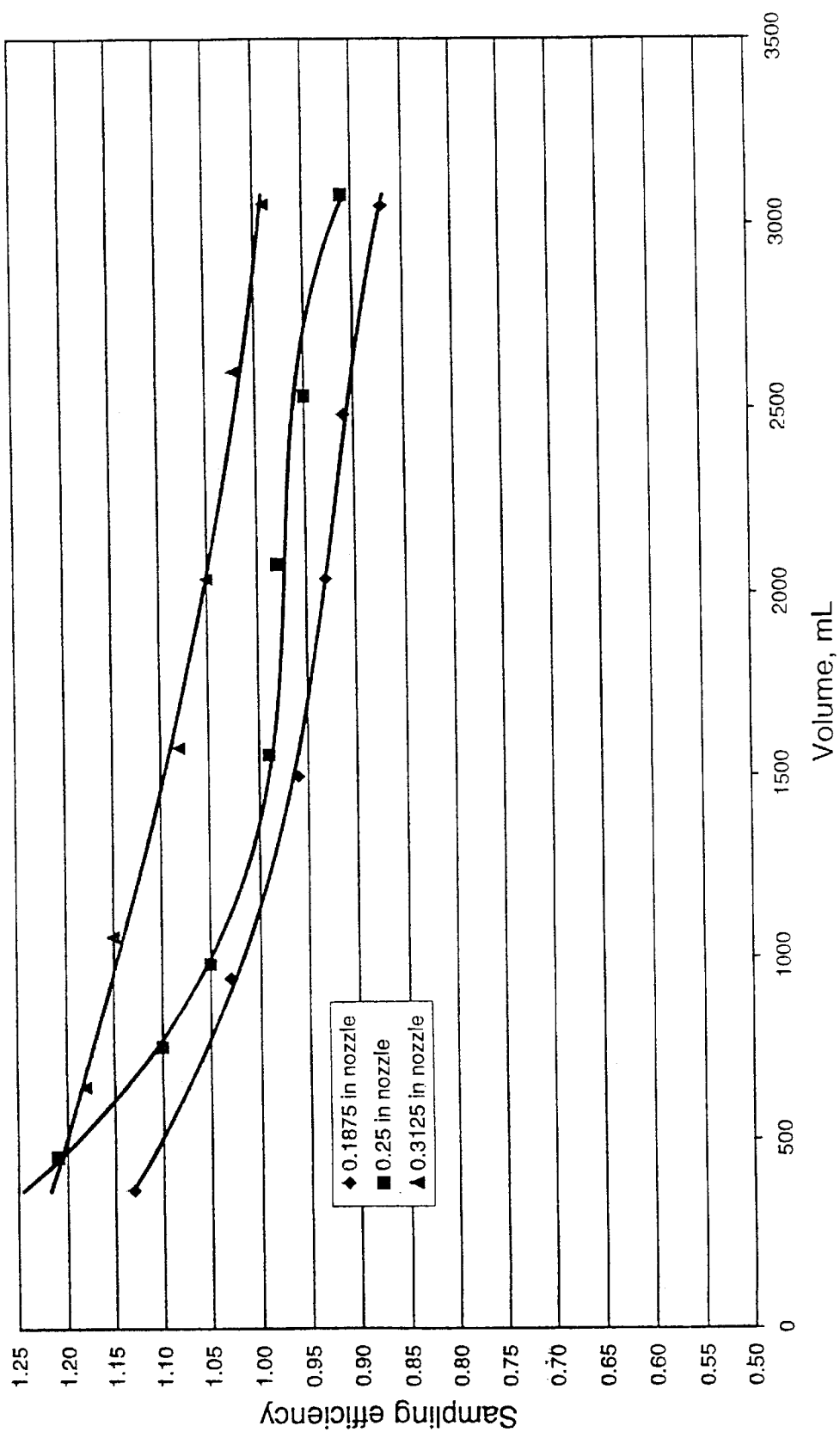
FIG. 13 shows the sampling efficiency of a sampler with a variety of nozzle sizes at 2 ft/sec flume velocity.
Figure 14:
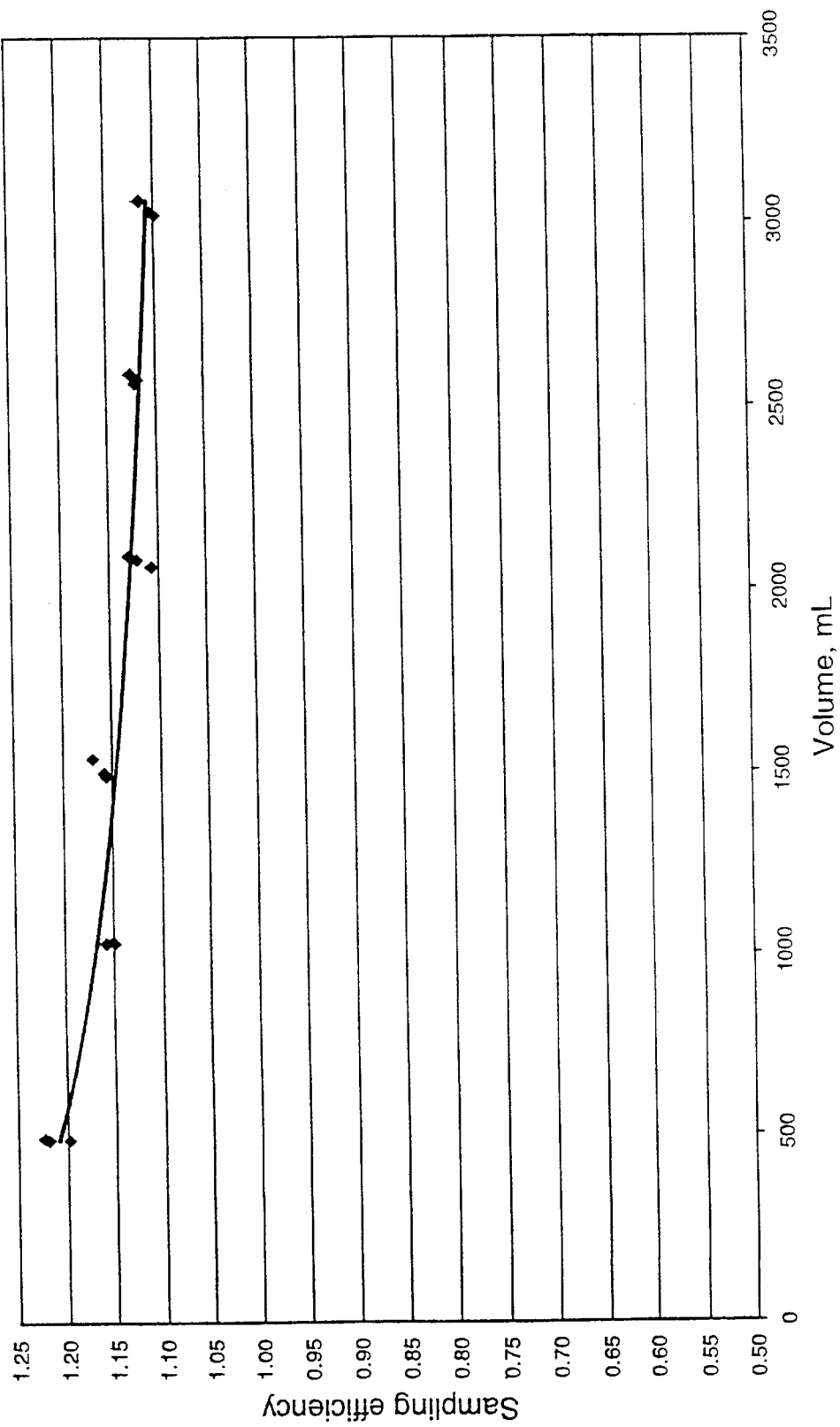
FIG. 14 shows the sampling efficiency of a sampler with a 0.1875 inch diameter nozzle at 3.65 ft/sec flume velocity.
Figure 15:
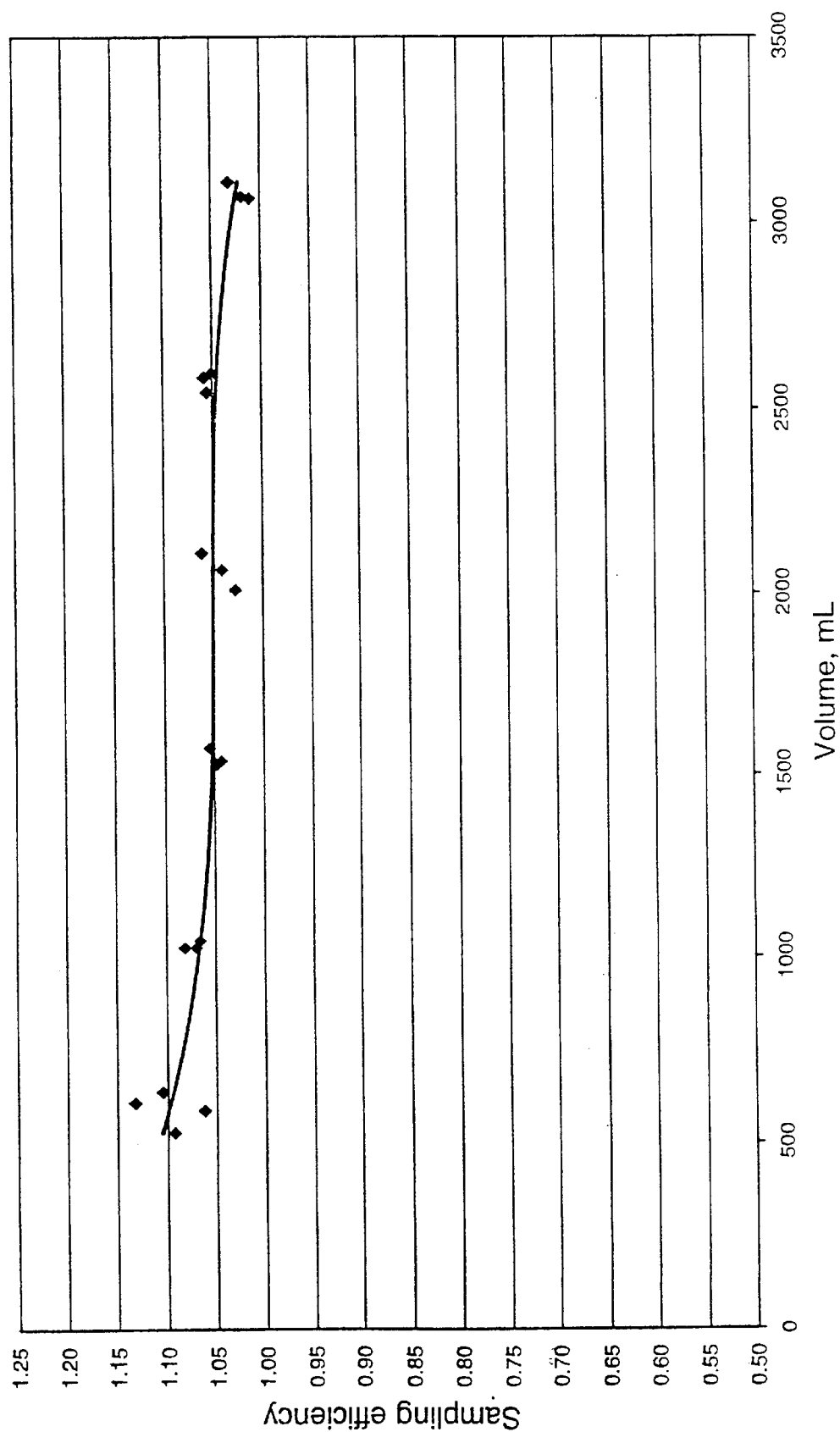
FIG. 15 shows the sampling efficiency of a sampler with a 0.25 inch diameter nozzle at 3.65 ft/sec flume velocity.
Figure 16:
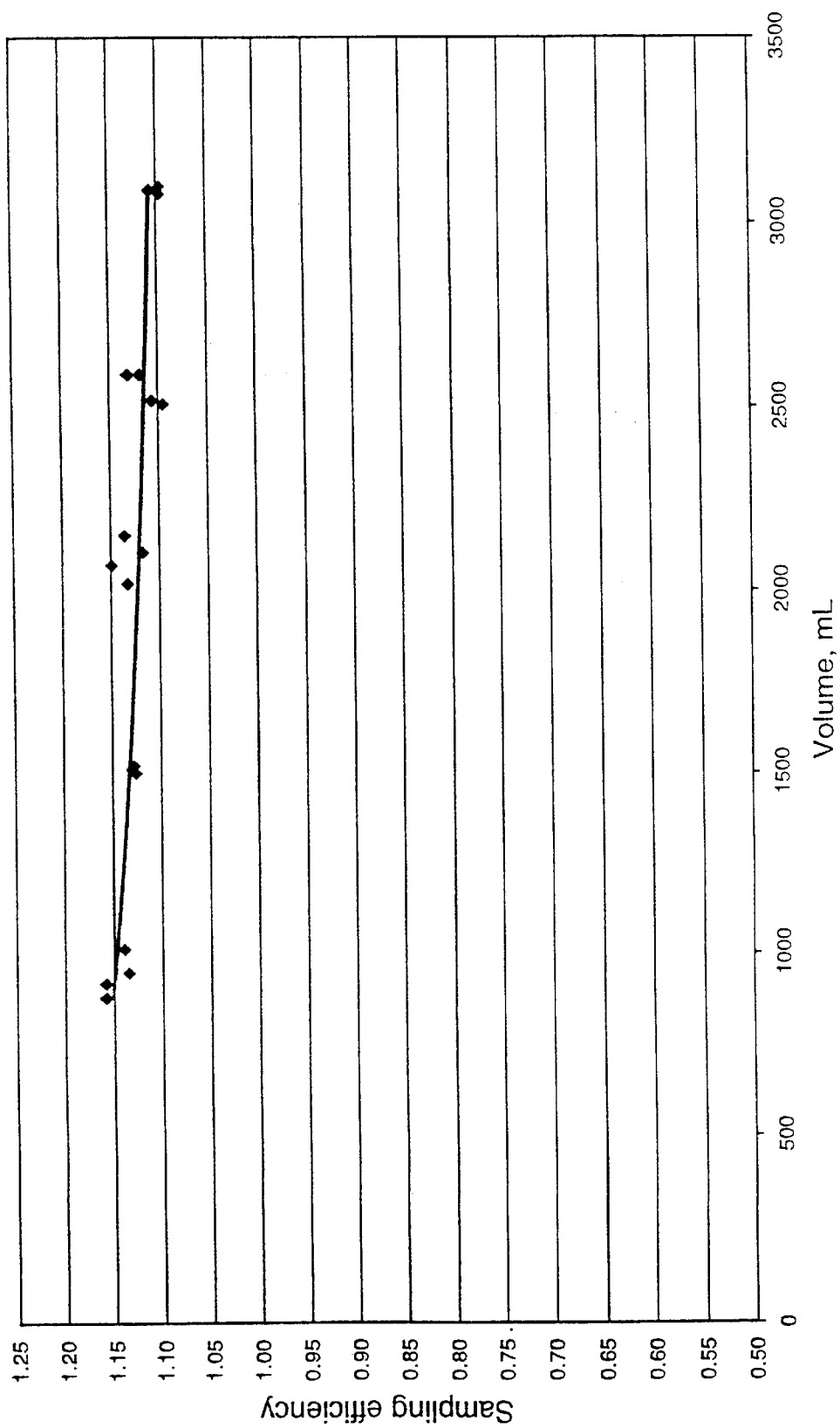
FIG. 16 shows the sampling efficiency of a sampler with a 0.3125 inch diameter nozzle at 3.65 ft/sec flume velocity.

The final design was based upon optimization of the parameters, and was subjected to tests with different nozzle diameters and flume velocities. The sampler was tested with 0.1875, 0.25 and 0.3125 inch diameter nozzles at 2.0, 3.65, and 5.0 ft/sec flume velocities. FIGS. 10, 11, and 12 show the results for a flume velocity of 2.0 ft/sec for the three nozzles. The figures show that the data are consistent and for the most part there is very little scatter of the data. The 0.1875 inch diameter nozzle, FIG. 10, had a sampling efficiency of 0.85 to 1.15 and collected over 3000 mL. The 0.25 inch diameter nozzle, FIG. 11, had a sampling efficiency of 0.90 to 1.10, except for the initial volume, and collected over 3000 mL. The 0.3125 inch diameter nozzle, FIG. 12, had a sampling efficiency of 1.00 to 1.15 with the exception of the initial volume, and collected over 3000 mL. FIG. 13 shows the average curves for the three nozzles at 2.0 ft/sec flume velocity.

Figure 17:
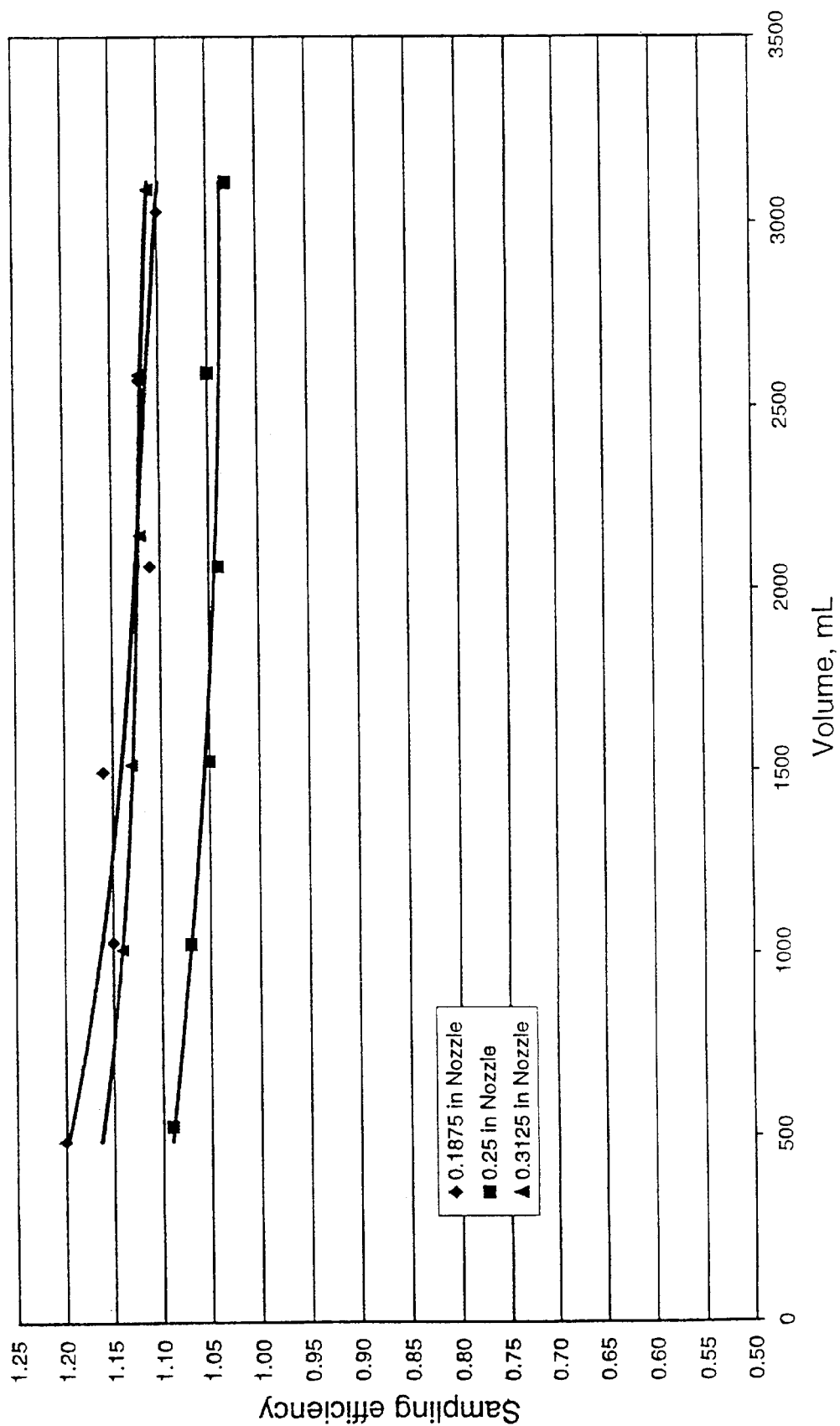
FIG. 17 shows the sampling efficiency of a sampler with a variety of nozzle sizes at 3.65 ft/sec flume velocity.
Figure 18:
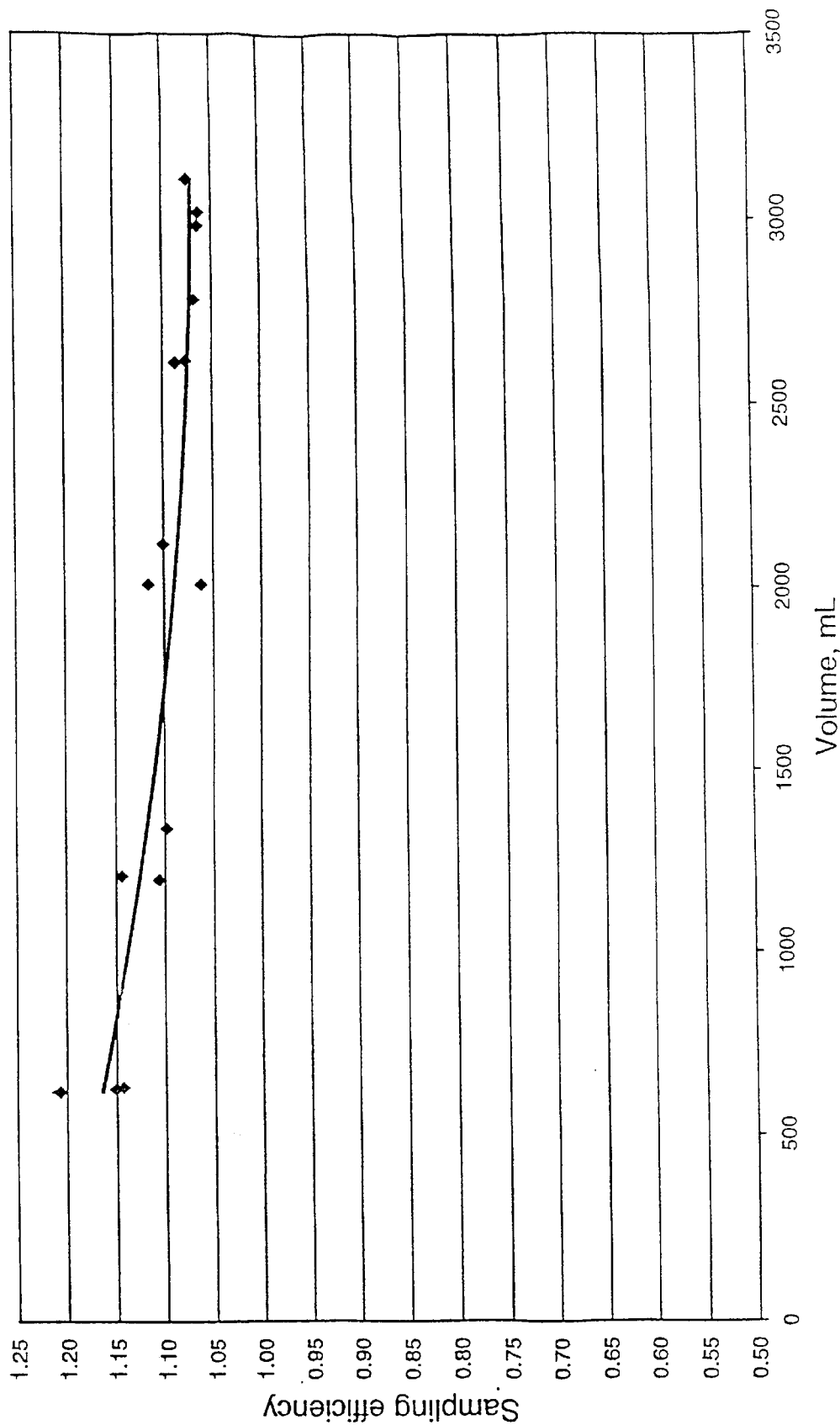
FIG. 18 shows the sampling efficiency of a sampler with a 0.1875 inch diameter nozzle at 5 ft/sec flume velocity.
Figure 19:
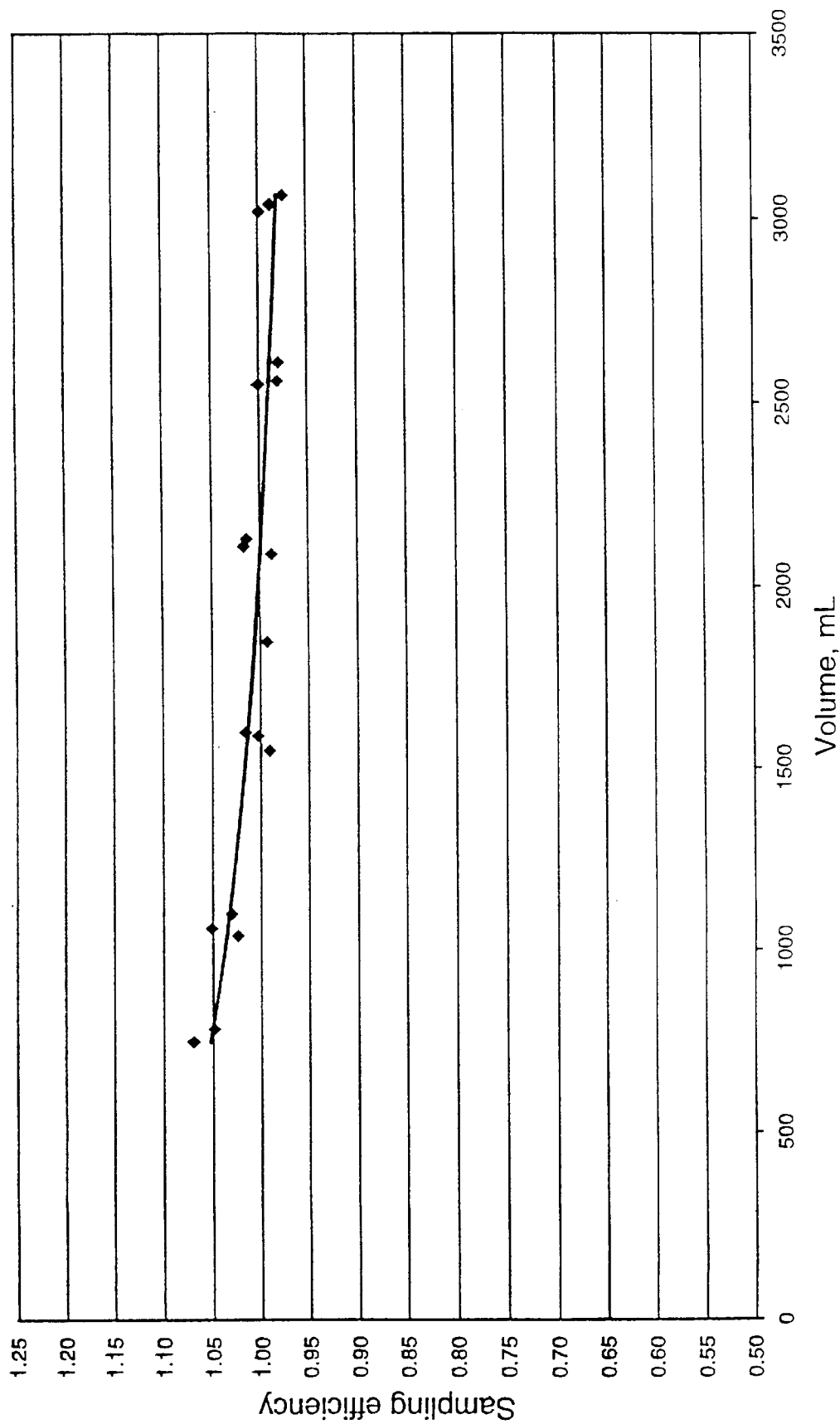
FIG. 19 shows the sampling efficiency of a sampler with a 0.25 inch diameter nozzle at 5 ft/sec flume velocity.
Figure 20:
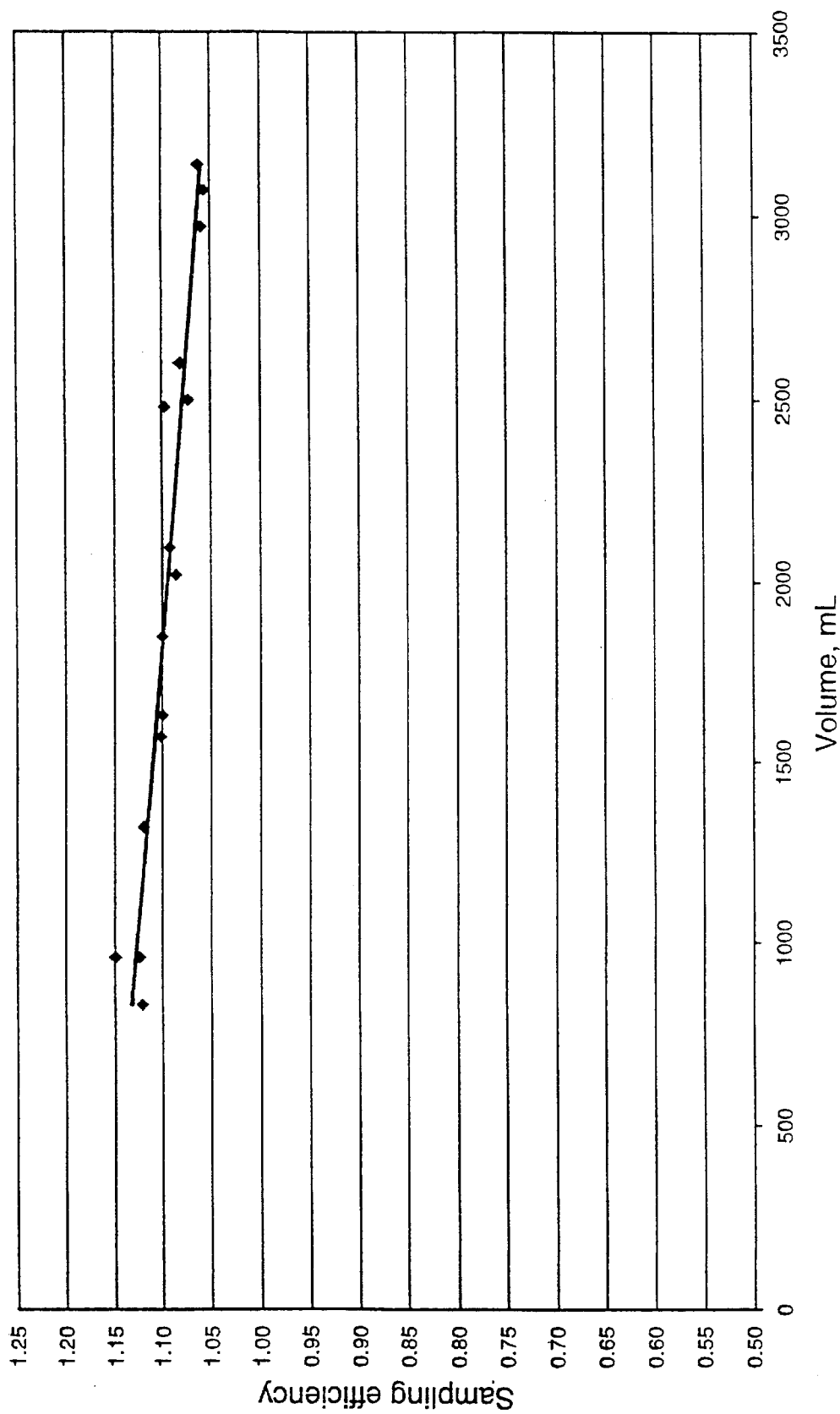
FIG. 20 shows the sampling efficiency of a sampler with a 0.3125 inch diameter nozzle at 5 ft/sec flume velocity.

FIGS. 14–17 show data for the three nozzles at a flume velocity of 3.65 ft/sec. The 0.1875 inch diameter nozzle, FIG. 14, had a sampling efficiency of 1.00 to 1.15, with the exception of the initial volume, and collected over 3000 mL of sample. The 0.25 inch diameter nozzle, FIG. 15, had a sampling efficiency of 1.00 to 1.10 and collected more than 3000 mL of sample. The 0.3125 inch diameter nozzle, FIG. 16, had a sampling efficiency of 1.10 to 1.15 and collected more than 3000 mL of sample. As can be seen from FIGS. 14–16 the sampling data were very consistent. FIG. 17 shows the average curve for the three nozzles at 3.65 ft/sec. flume velocity.

Figure 21:
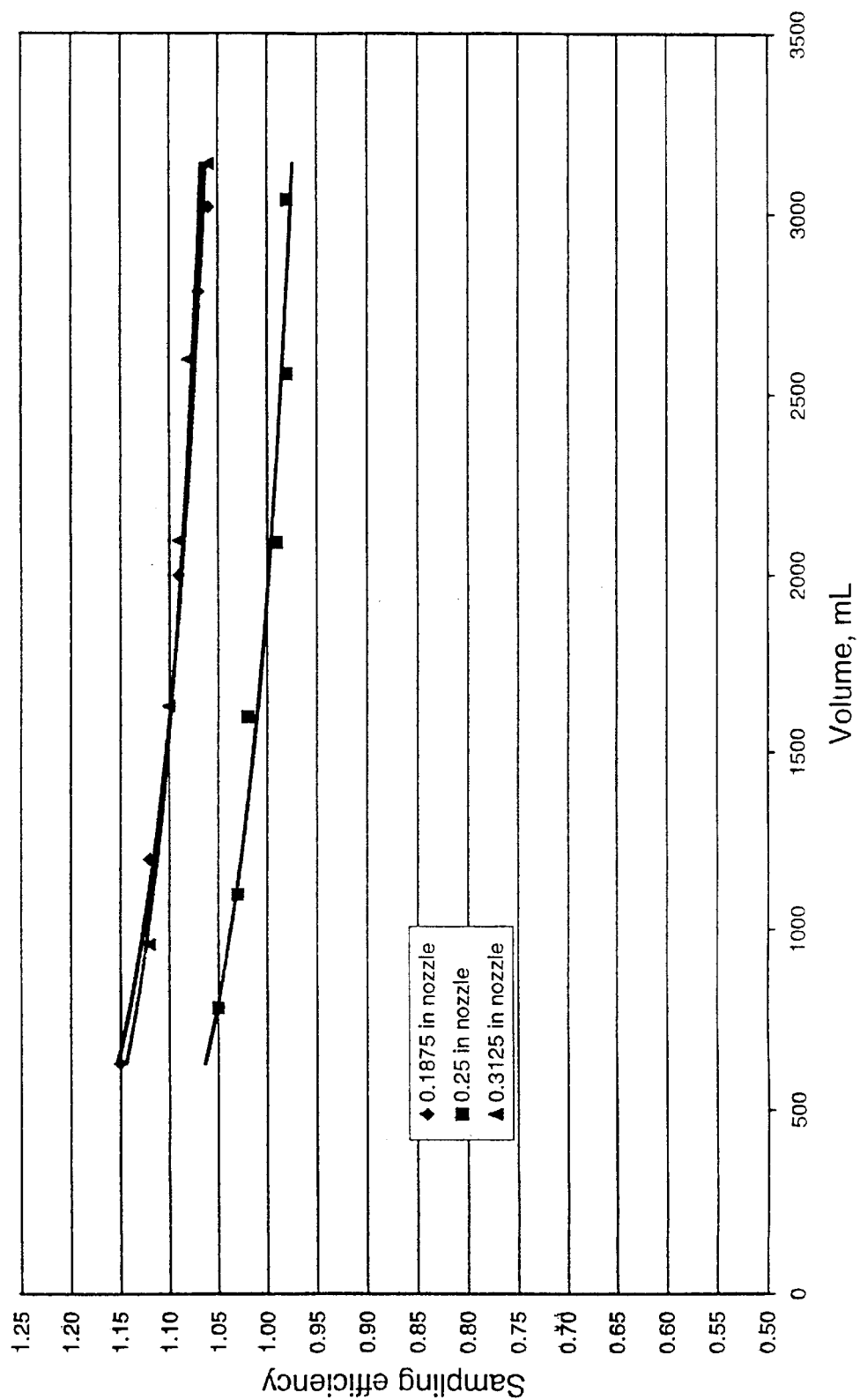
FIG. 21 shows the sampling efficiency of a sampler with a variety of nozzle sizes at 5 ft/sec flume velocity.

FIGS. 18–21 show data for the three nozzles at a flume velocity of 5.0 ft/sec. The 0.1875 inch diameter nozzle, FIG. 18, had a sampling efficiency of 1.06 to 1.15 and collected over 3000 mL of sample. The 0.25 inch diameter nozzle, FIG. 19, had a sampling efficiency of 0.97 to 1.05 and collected more than 3000 mL of sample. The 0.3125 inch diameter nozzle, FIG. 20, had a sampling efficiency of 1.05 to 1.15 and collected more than 3000 mL of sample. As can be seen from FIGS. 18–20, the sampling data were very consistent. FIG. 21 shows the average curve for the three nozzles at 5 ft/sec flume velocity.

An additional method for assessing the operation of the sampler is by determining the average sampling efficiency in the collection of a full sample. The average efficiency should be within the acceptable range of 1.00 plus or minus 0.15. Table 1 shows the average sampling efficiency for the three nozzles at three flume velocities. The efficiencies are well within the acceptable range, with most between 0.90 and 1.10. The results shown in the figures and the table clearly indicate that the sampler met the operational goals. Other preliminary tests indicate that the sampler may operate effectively at stream velocities up to 10 ft/sec.

TABLE 1

| Nozzle Diameter (inches) | Flume Velocity (ft/sec) | Sample Volume (mL) | Efficiency |
| --- | --- | --- | --- |
| 3/16 | 2.00 | 3050 | 0.87 |
| 1/4 | 2.00 | 3080 | 0.91 |
| 5/16 | 2.00 | 3050 | 0.99 |
| 3/16 | 3.65 | 3030 | 1.10 |
| 1/4 | 3.65 | 3110 | 1.03 |
| 5/16 | 3.65 | 3090 | 1.11 |
| 3/16 | 5.00 | 3020 | 1.06 |
| 1/4 | 5.00 | 3040 | 0.98 |
| 5/16 | 5.00 | 3140 | 1.06 |

Flume tests also showed that the sampler quickly oriented itself to face into the stream flow. The sampler was very stable, keeping the nozzle horizontal even at the higher velocities tested.

Another important feature of the sampler of the present invention is the depth to which the sampler can be used for collecting sediment, and the rate at which the sampler can be lowered and raised. By collecting a full three liters of sample, the sampler as designed and tested can sample to a depth of 39 feet with a 0.3125 inch diameter nozzle, 62 feet with a 0.25 inch diameter nozzle, and 110 feet with a 0.1875 inch diameter nozzle. The rate at which the sampler can be lowered and raised is limited only to a maximum of 0.4 times the stream velocity.

The sampler of the present invention provides many advantages over previously disclosed samplers. The sampler can be used to a much greater depth than rigid body depth-integrating samplers. The sampler of the present invention can be used to a depth of 110 feet, whereas the rigid body sampler can only be used to depths of 15 feet.

There is no limitation in transit rate due to air compressibility problems as is the case with rigid body samplers. The sampler of the present invention was specifically designed to use flexible bags, whereas previously investigated bag samplers were merely modifications of rigid bottle samplers.

The sampler of the present invention can sample isokinetically at much lower stream velocities, i.e., 2 ft/sec, which is the minimum velocity at which sand-sized particles are suspended in the water column, than previously investigated bag samplers, which were only able to sample at stream velocities of over 3 ft/sec.

The sampler of the present invention can collect a full three liters of sample. Previously investigated bag samplers collect only approximately 80 pct of rated capacity.

The sampler of the present invention has a smaller unsampled zone, 4 inches, than previously investigated bag samplers, which had unsampled zones of 7 inches and up to 18 inches.

The sampler of the present invention is consistent in operation. Previously investigated bag samplers were found not to sample for no apparent reason.

The sampler of the present invention is much simpler to use than previously investigated bag samplers. The bag is easily removed from the sampler body.

The sampler of the present invention has unlimited application in sediment and/or water quality sampling and collecting water for trace element analysis. Previous samplers are limited to specific applications.

All references cited herein, including journal articles or abstracts, published or unpublished U.S. or foreign patent applications, issued U.S. or foreign patents, or any other references are entirely incorporated by reference herein, including all data, tables, figures, and text present in the cited references. Additionally, the entire contents of the references cited within the references cited herein are also incorporated by reference in their entirety.

References to known method steps, conventional method steps, known methods or conventional methods is not in any way an admission that any aspect, description, or embodiment of the present invention is disclosed, taught, or suggested in the relevant art.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

References

Edwards and Glysson, "Field Methods for Measurement of Fluvial Sediment", U.S. Geological Survey Open-File Report 86–531, pp. 5–7 (1988).

Federal Interagency Sedimentation Project "Field Practice and Equipment used in Sampling Suspended-Sediment", Interagency Report 1 (Minneapolis, Minn., St. Anthony Falls Hydraulic Laboratory), pp. 154–155.

Federal Interagency Sedimentation Project, "Laboratory Investigations of Suspended-Sediment Samplers", Interagency Report No. 5 (Minneapolis, Minn., St. Anthony Falls Hydraulic Laboratory), p. 99 (1941).

Federal Interagency Sedimentation Project, "The Design of Improved Types of Suspended-Sediment Samplers", Interagency Report 6 (Minneapolis, Minn., St. Anthony Falls Hydraulic Laboratory). pp. 22–24, 33–34 (1952).

Meade, Robert H., Ed., "Contaminants in the Mississippi River", U.S. Geological survey circular 1133, Reston, Va.

Szalona, J. J., "Development of a Bag-Type Suspended-Sediment Sampler", Interagency Report Y (Minneapolis, Minn., St. Anthony Falls Hydraulic Laboratory), p. 32 (1982).

Stevens et al, "Collapsible-Bag Suspended-Sediment Sampler", *Journal of the Hydraulics Division, ASCE* 106 (HY4):611–616 (1982).

What is claimed is:

1. A sampler for sampling water in flowing bodies of water comprising:

a top section;

a bottom section connected to said top section;

a tail section having fins, which tail section is fitted onto said top section;

a nose section with tray, which tray supports a flexible bag;

a nozzle holder;

a nozzle holder insert in said top section to hold the nozzle;

a flexible bag attached to the outside of the rear of the nozzle holder.

2. The sampler according to claim 1, wherein said tail section has horizontal fins and vertical fins.

3. The sampler according to claim 1, wherein said top section is made of a material which supplies most of the weight to the sampler.

4. The sampler according to claim 1, wherein said nozzle holder includes a pressure equalization hole.

5. The sampler according to claim 1, wherein said tail section is made of a neutrally buoyant material.

6. The sampler according to claim 5, wherein said neutrally buoyant material is high density polyethylene.

7. The sampler according to claim 1, wherein said tray slides for removal or insertion of the flexible bag.

8. The sampler according to claim 1, wherein a vent hole is provided in the top of the sampler.

9. The sampler according to claim 1, wherein a vent hole is provided in the top of the sampler with a deflector.

10. The sampler according to claim 1, wherein a vent hole is provided in the top of the sampler with a deflector.

11. The sampler according to claim 1, wherein a vent hole is provided in the top and in the bottom of the sampler with a deflector.

* * * * *